(12) United States Patent
Turner et al.

(10) Patent No.: US 10,849,579 B2
(45) Date of Patent: Dec. 1, 2020

(54) SUPPORT STAND FOR A PORTABLE X-RAY IMAGING DEVICE

(71) Applicant: Turner Imaging Systems, Inc., Orem, UT (US)

(72) Inventors: D. Clark Turner, Payson, UT (US); Thomas L. Youd, Salt Lake City, UT (US); Casey Messick, Pleasant Grove, UT (US)

(73) Assignee: Turner Imaging Systems, Inc., Orem, UT (US)

( * ) Notice: Subject to any disclaimer, the term of this patent is extended or adjusted under 35 U.S.C. 154(b) by 0 days.

(21) Appl. No.: 16/198,956

(22) Filed: Nov. 23, 2018

(65) Prior Publication Data
US 2020/0163634 A1    May 28, 2020

(51) Int. Cl.
*A61B 6/00*    (2006.01)

(52) U.S. Cl.
CPC ............ *A61B 6/4405* (2013.01); *A61B 6/447* (2013.01); *A61B 6/4411* (2013.01); *A61B 6/4441* (2013.01); *A61B 6/4452* (2013.01)

(58) Field of Classification Search
CPC ... A61B 6/4405; A61B 6/4411; A61B 6/4441; A61B 6/4452; A61B 6/447
See application file for complete search history.

(56) References Cited

U.S. PATENT DOCUMENTS

| 2008/0123819 | A1* | 5/2008 | Jensen | A61B 6/4405 378/198 |
| 2011/0049370 | A1* | 3/2011 | Yoshida | A61B 6/4405 250/354.1 |
| 2011/0306864 | A1* | 12/2011 | Zarate | A61B 6/4405 600/407 |
| 2017/0065246 | A1* | 3/2017 | Lee | A61B 6/08 |

* cited by examiner

Primary Examiner — Mark R Gaworecki
(74) Attorney, Agent, or Firm — Kenneth E. Horton; Kirton McConkie

(57) ABSTRACT

Supporting devices for small and portable X-ray devices are described. In particular, this application describes supporting devices for portable X-ray devices containing a movable base unit with multiple legs with different lengths and heights configured so that the legs have a nestable configuration, an adjustable member extending from the mobile base unit so the adjustable member has an adjustable height, an extension arm connected to the adjustable member so the extension arm collapses toward and extends away from the adjustable member, and a connecting member connecting the extension arm with a portable x-ray device so the connecting member can rotate up to 360 degrees in the x, y, or z direction. The connecting member can also connect the extension arm with a portable x-ray device so the portable x-ray device is removable from the connecting member and capable of being operated independently by hand. Other embodiments are described.

21 Claims, 19 Drawing Sheets

SUPPORT STAND FOR A PORTABLE X-RAY IMAGING DEVICE

FIELD

This application relates generally to X-ray equipment. More specifically, this application relates to support stands that are used to assist with operating small and portable x-ray devices.

BACKGROUND

X-ray imaging systems typically contain an X-ray source and an X-ray detector. X-rays (or other type of radiation) is emitted from the source and impinges on the X-ray detector to provide an X-ray image of the object or objects that are placed between the X-ray source and the detector. The X-ray detector is often an image intensifier or even a flat panel digital detector. In some configurations, these devices are supported on a C-arm assembly with the source and detector on opposite ends of the "C" arm of the assembly. The C-arm assembly can move through continuous rotation or orientation angles relative to the object in order to acquire images from multiple orientations.

Traditional X-ray imaging systems have limited mobility since they are supported on a gantry that is secured to a floor, wall, or ceiling. Other imaging systems are more portable since they are supported on a mobile base (on wheels) so they can be used in and moved to a variety of clinical environments, such as radiology and surgery departments of a medical facility.

SUMMARY

This application relates generally to support stands that are used to assist with the operation and use of small and portable x-ray devices. In particular, this application describes a supporting device for a portable X-ray device that contains a movable base unit containing multiple legs with different lengths and heights configured so that the legs have a nestable configuration, an adjustable member extending from the mobile base unit where the adjustable member is configured with an adjustable height, an extension arm connected to the adjustable member where the extension arm is configured to collapse toward and extend away from the adjustable arm, and a connecting member configured to connect the extension arm with a portable x-ray device where the connecting member is able to rotate up to 360 degrees in the x, y, or z direction. The connecting member can also be configured to connect the extension arm with a portable x-ray device so that the portable x-ray device is removable from the connecting member and capable of being operated independently by hand. X-ray systems that contain such a supporting device and such a portable x-ray device are light and easy to move from location to location by medical personnel. The x-ray systems are also extremely versatile during medical procedures because the support device provides a wide range of motion for images to be taken of a patient using the portable x-ray device.

BRIEF DESCRIPTION OF THE DRAWINGS

The following description can be better understood in light of the Figures which show various embodiments and configurations of the X-ray devices.

Figure 1:
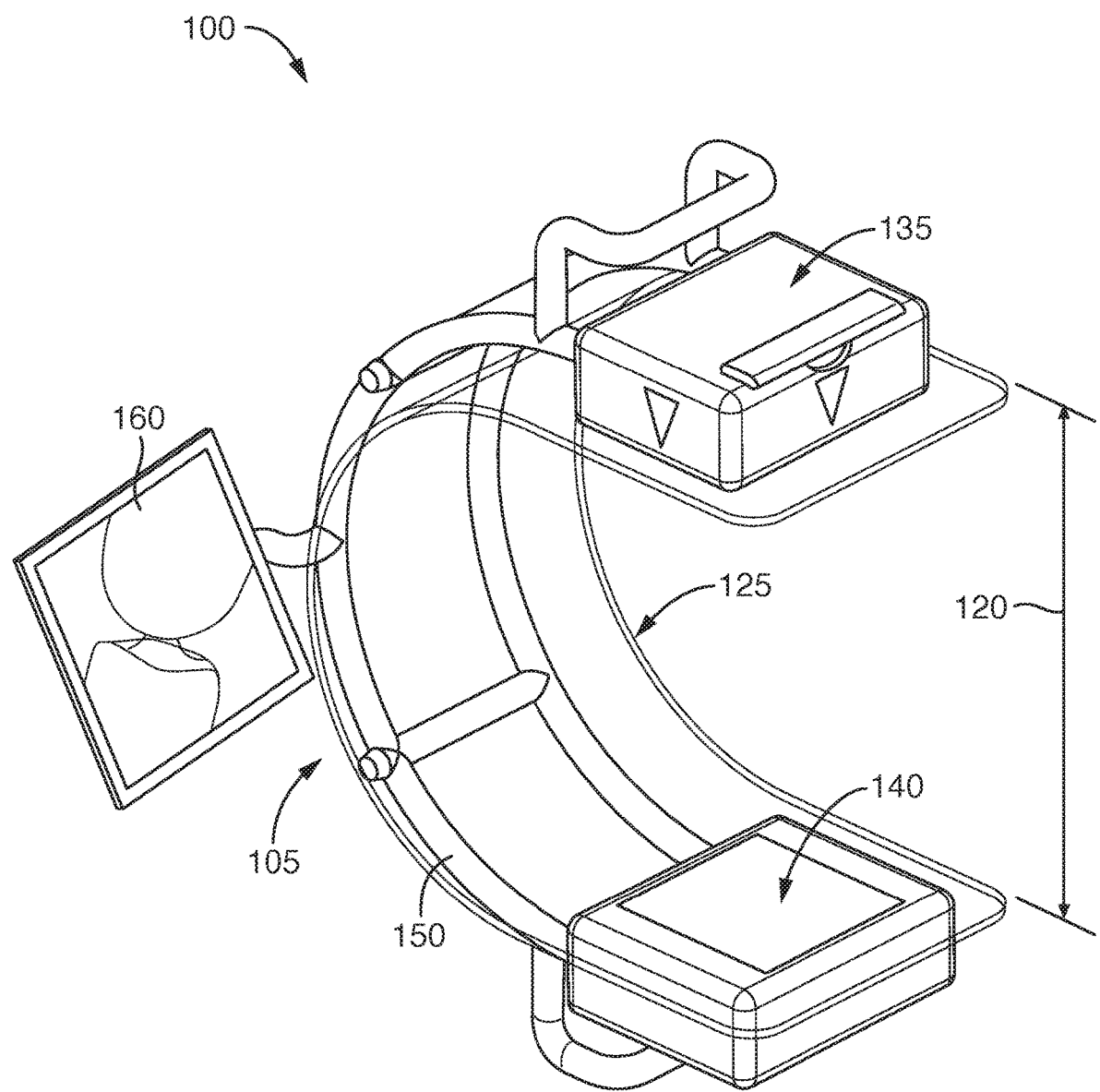
FIG. 1 shows a view of some embodiments of small, portable X-ray devices.

Together with the following description, the Figures demonstrate and explain the principles of the structures, methods, and systems described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray devices can be implemented and used without employing these specific details. Indeed, the described systems and methods for controlling and positioning X-ray devices can be placed into practice by modifying the described systems and methods and can be used in conjunction with any other imaging apparatus (potentially even imaging using other forms of radiation such as visible light, infra-red light, gamma rays, and even ultrasound) and techniques conventionally used in the industry. For example, while the description below focuses on support stands for small, portable C-arm x-ray devices, the support stands can be used with other X-ray imaging arms and x-ray devices, including U-arms or portable x-ray devices that are configured to approximate the C-arm configuration.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

FIG. 1 shows some embodiments of small, portable X-ray devices 100 that can be attached to and held by the supporting devices described herein. Generally, the portable X-ray devices 100 contain an imaging arm that allows the devices to be used to take X-ray images of a portion of a patient's body or any other object capable of being analyzed by x-rays, including animals, industrial components such as electronic circuit boards, containers to be inspected, and/or passenger luggage. In some configurations, the imaging arm is substantially shaped like the letter "C" and is therefore referred to as a C-shaped support arm (or C-arm) 105. The C-arm has any size that can be held and operated by hand when in use, as seen in FIG. 1.

The C-arm 105 can contain any X-ray source 135 and X-ray detector 140 that allow the X-ray system 100 to take X-ray images. The X-ray source 135 can contain any source that generates and emits X-rays, including a standard stationary anode X-ray source, microfocus x-ray source, rotating anode x-ray source, and/or a fluoroscopic X-ray source. And the X-ray detector 140 can contain any detector that detects X-rays, including an image intensifier, CMOS camera and/or a digital flat panel detector. In some configurations, the detector can have a substantially square shape with a length ranging from about 12 cm to about 20 cm. The X-ray source 135 can be contained in a housing that can be configured in two parts with a first part enclosing the x-ray source 135 and a second, separate part enclosing the x-ray detector 140. In other configurations, however, the housing can be configured so that it is a single part that encloses both the X-ray source 135 and the X-ray detector 140.

In some configurations, the housing can also enclose a removable power source (such as a battery) and optionally a power supply. Thus, the power source and the power supply can be located internal to the housing and also to the x-ray device 100. The supporting electronics for the power source and the power supply, as well as the supporting electronics for an image display and for wireless data upload, can also be located internal to the housing. Thus, in these configurations, the x-ray device 100 does not contain an external power cord. Incorporating the power source (i.e., the battery), the power supply, and the supporting electronics all within the housing allows the size and the weight of the device to be reduced, and also eliminates the electrical cables that would otherwise be required to connect the X-ray source and detector to power and data handling and gathering components such as computers. Of course, if needed, the x-ray device 100 can be configured so that it is alternately, or additionally, charged using external power from a power cord that is plugged into a wall outlet. In other configurations, multiple power supplies can be provided for the source, detector, and control electronics, any (or all) of which can be located either internal or external to the housing.

The X-ray device 100 also contains a frame 150 that has an open configuration. As shown in FIG. 1, an open configuration gives a number of easy gripping options for a user to carry and hold the frame 150 during transport, and optionally during operation of the x-ray device 100. In some embodiments, the frame 150 can be configured as a modular unit so different cross members (or length member or handles) can be used to replace the existing cross members (or length member or handles). Thus, the frame 150 provides the ability for a user (or operator) to grip and hold the X-ray device 100 during operation, a feature that is useful since other conventional C-arms can't be held in the hands while being operated because they do not have a frame and because they are too heavy.

Figure 2:
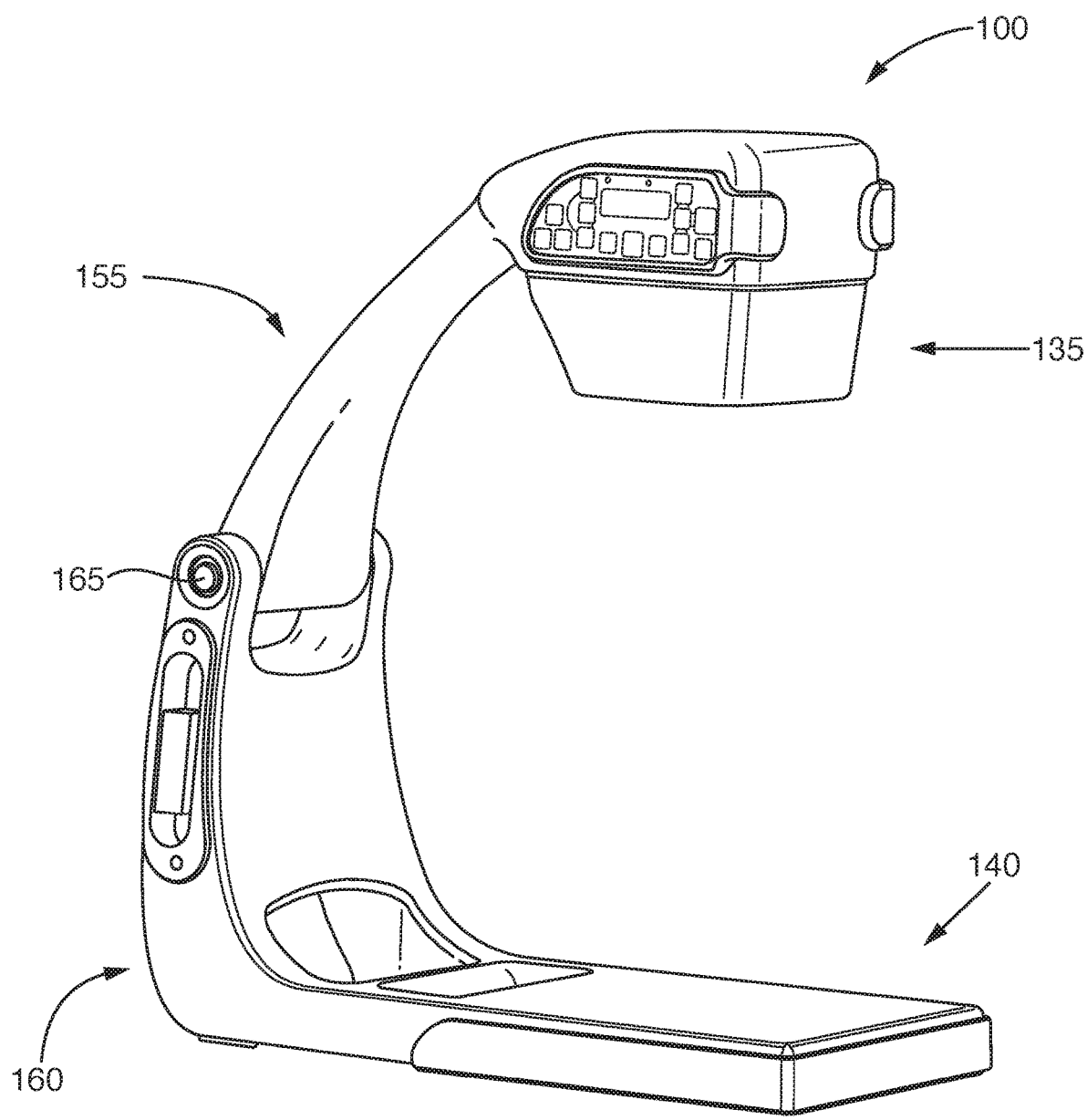
FIG. 2 shows another view of some embodiments of small, portable X-ray devices.

In other embodiments, the portable x-ray device 100 has the configuration as illustrated in FIG. 2. In the embodiments of FIG. 2, the frame 150 had a first portion 155 that is part of the housing that also contains the x-ray source and the associated electronics. The frame 150 also has a second portion 160 that is part of the housing that also contains the x-ray detector and the associated electronics. The first portion 155 of the housing and the second portion 160 of the housing are connected using lockable hinge 165.

The portable x-ray device 100 has several features not exhibited by other C-arm devices. First, it has the capability of a wireless data transfer, thereby eliminating the need for any wired connections or cables to the C-arm 105. Second, it is internally powered by a battery or internal power source and, therefore, more portable than other C-arm devices which require a power cable. Third, it is lighter than other C-arm devices. As a comparison, the portable x-ray C-arm devices 100 described herein can have a weight ranging from about 10 to about 25 pounds while other C-arm devices have a weight ranging from about 35 to about 400 pounds. In other embodiments, the portable x-ray C-arm devices 100 described herein can have a weight ranging from about 12 to about 18 pounds.

Figure 3A:
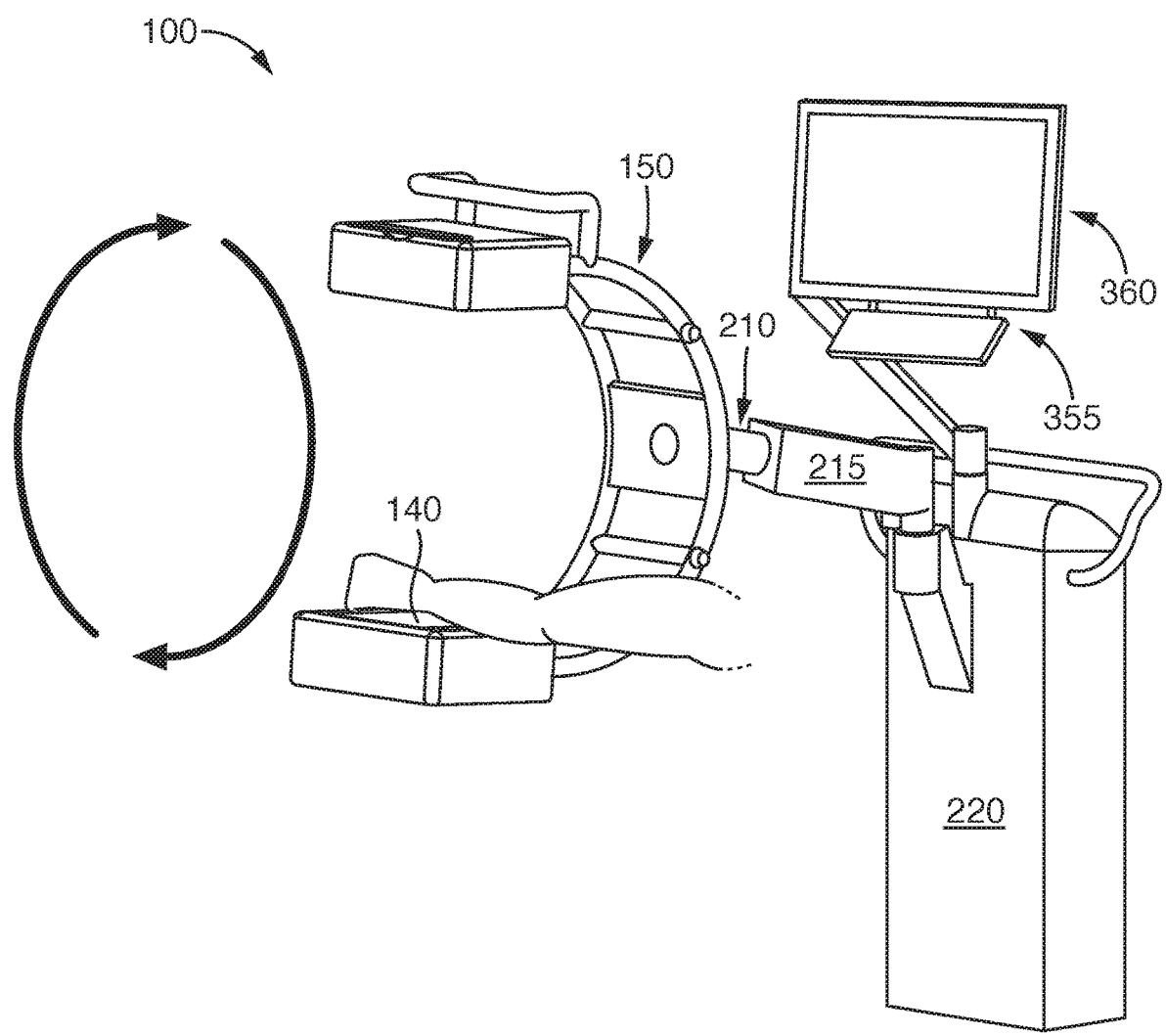
FIGS. 3A and 3B show some embodiments of supporting devices that can be used with small, portable X-ray devices.
Figure 3B:
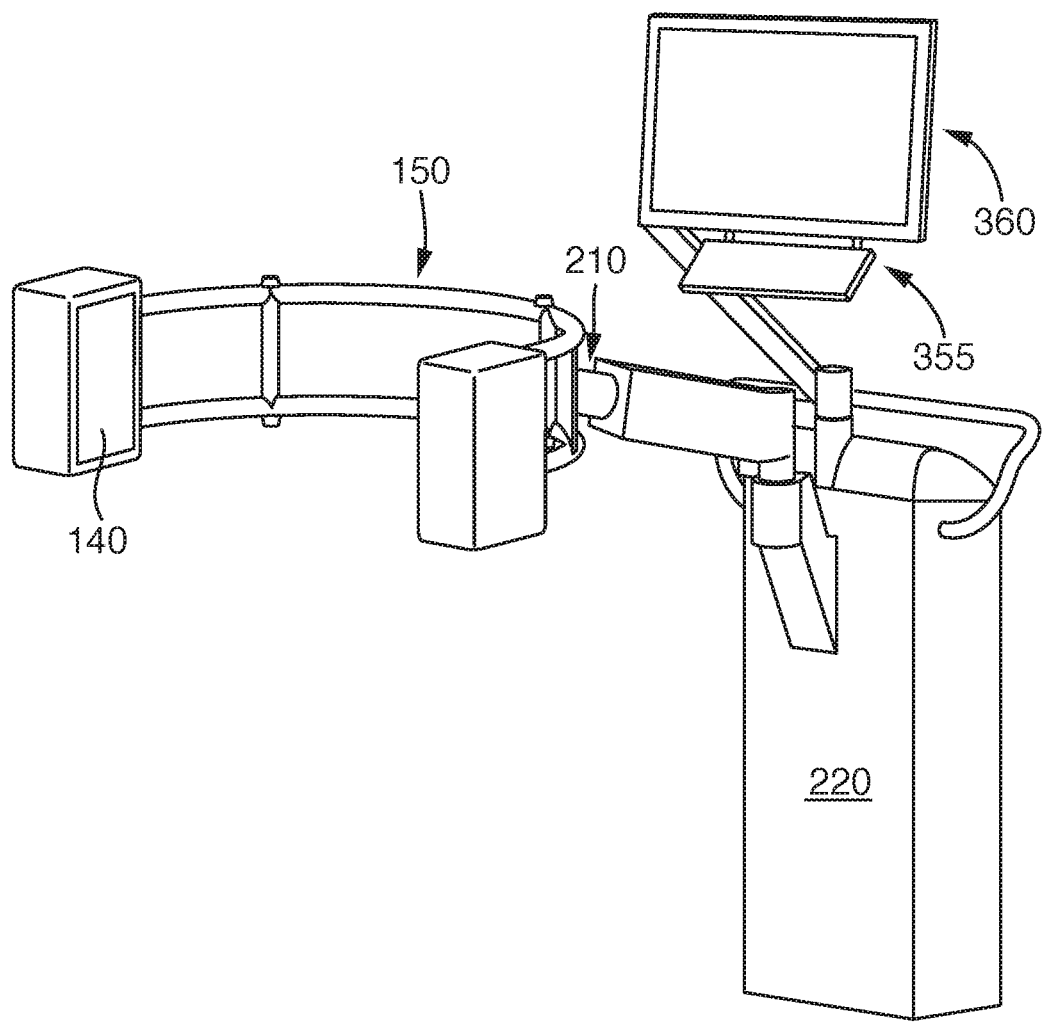

In some configurations, the portable x-ray device 100 can be connected to a stationary external (or support) structure so that it can rotate around an object being analyzed, as shown in FIGS. 3A and 3B. In these embodiments, the connection between the frame 150 and the external structure contains triple function joint (or tri-joint) 210 that allows the following three functions. First, the tri-joint 210 can be attached to the C-arm 105 and the support structure so that the C-arm 150, similar to other conventional C-arms, can rotate around the object (i.e., from the position in FIG. 3A to the position in 3B) being analyzed (i.e., the arm of a patient). Second, the tri-joint 210 allows the X-ray device to be quickly and easily attached (and detached) from the external structure. And third, the tri-joint 210 allows the connection between the X-ray device 100 and the external structure to be located at any desired location of the frame (i.e., at 15, 30, 45, 60, 75, 90, 105, 120, 135, 150, and 165 degrees along the arc of the C-arm, or at any located therebetween). For example, as shown in FIG. 3A the tri-joint 210 is connected to x-ray device 100 at about 90 degrees along the arc of the C-arm while in FIG. 3B the tri-joint 210 is connected to x-ray device 100 at about 60 degrees.

FIGS. 3A and 3B shows some embodiments in which the tri-joint 210 is attached at one end to the frame 150 of X-ray device 100 and at the other end to an extension 215 that extends from the external structure. In the embodiments shown in FIGS. 3A and 3B, the external structure comprises a supporting base 220 to which the extension 215 is connected. In some embodiments, the support structure can also contain any other medical components and electronic components, like the display 360 and the user interface 355. In some configurations, the X-ray device 100 can be covered with a surgical drape for surgical procedures.

Figure 14:
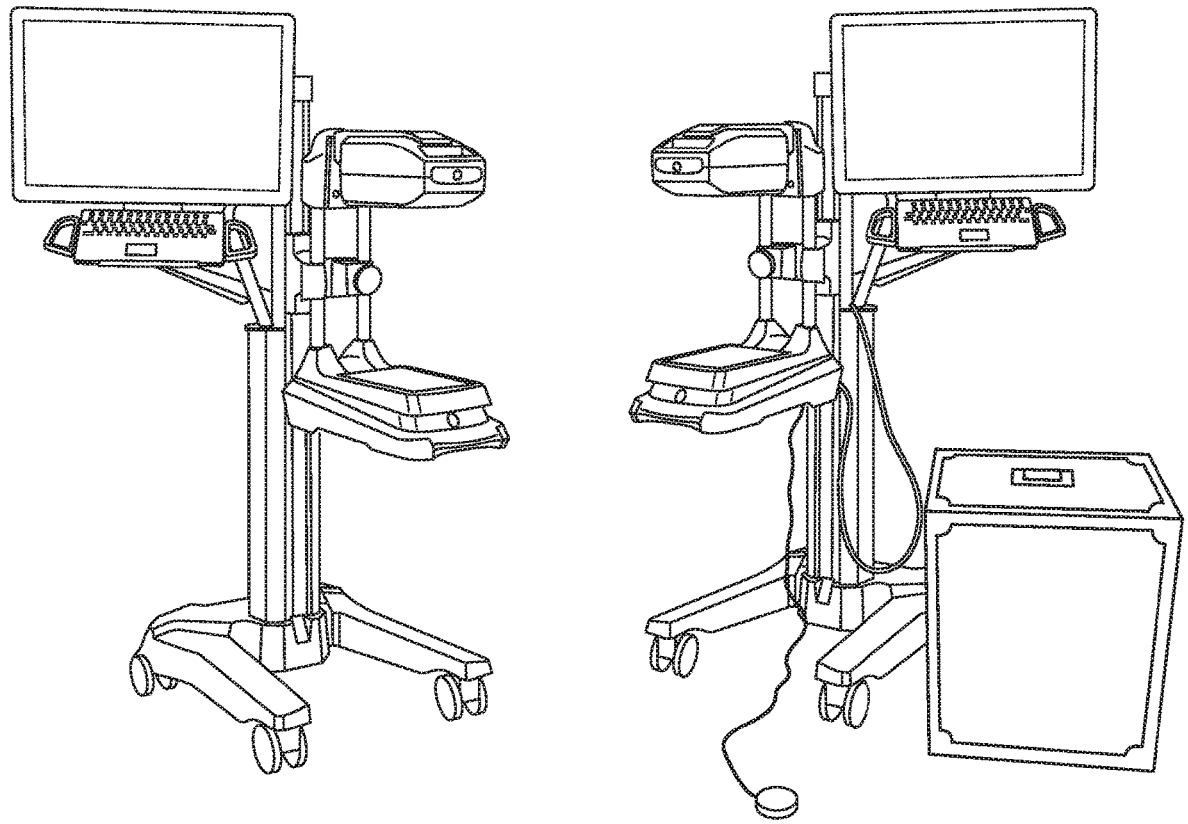
FIGS. 14-15 show some conventional supporting devices for x-ray devices.
Figure 15:
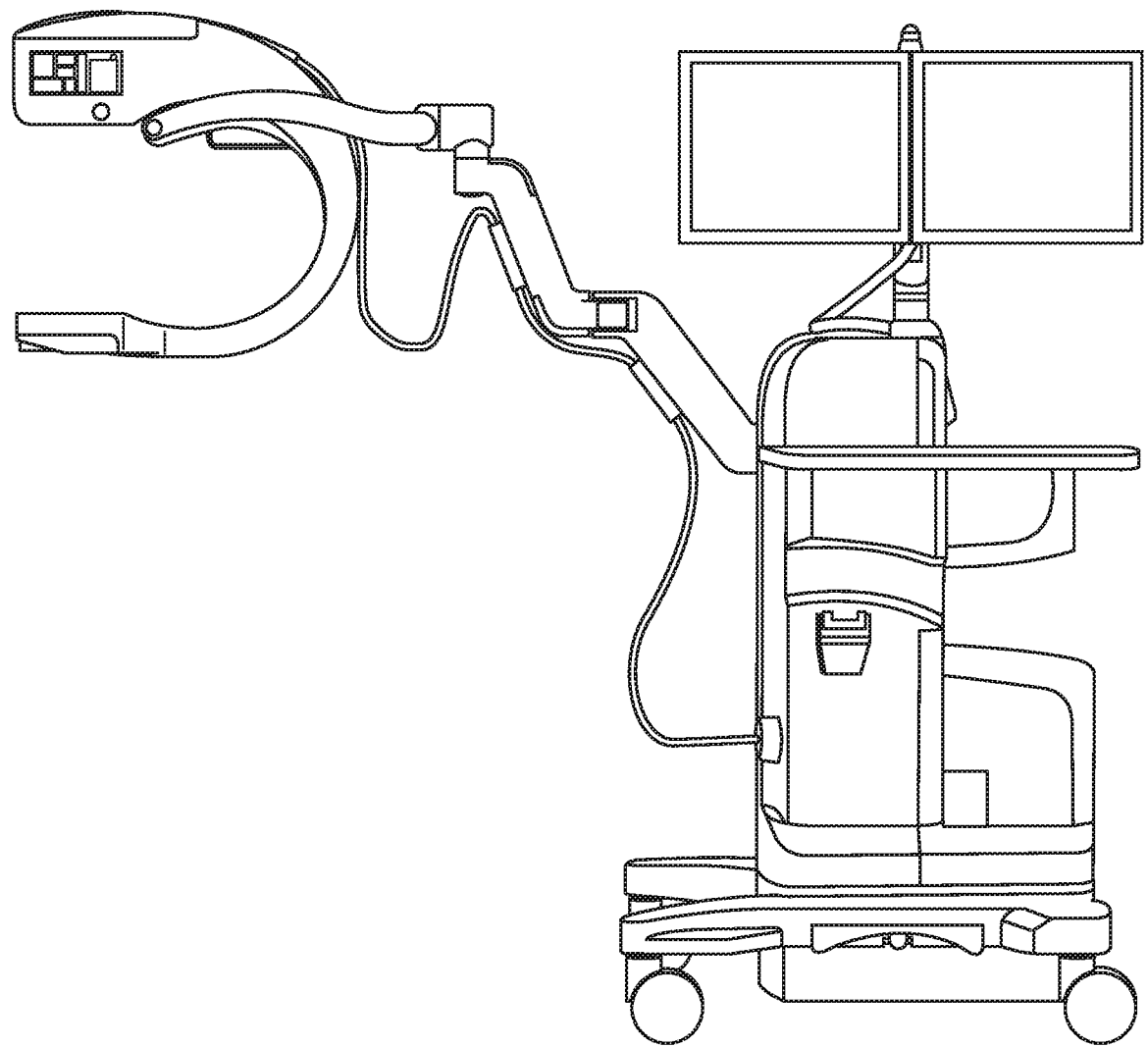

These configurations shown in FIGS. 3A and 3B differ slightly from some conventional x-ray systems with a C-arm x-ray device connected to external support structures, as shown in FIGS. 14-15. These conventional X-ray systems suffer from several problems. First, they are heavy and cumbersome. For example, these X-ray systems (with wheels) can weigh up to 350 pounds or more and, therefore, are hard to move across the floor since they require a major effort to push them. So these x-ray systems are often stationed in one location and left there, getting in the way of the medical personnel and the patient during a medical procedure. So while these x-ray systems in FIG. 14-15 are capable of being moved, in reality their mobility is very limited. A second problem with the X-ray systems shown in FIGS. 14-15 is that they contain control, data, and power cables. These cables, especially the power cables, connect the X-ray devices to a separate power source which converts power from a wall outlet into specialized high voltage electrical power. This separate power source must be plugged into fixed locations (i.e., a wall outlet), further limiting the mobility of the entire x-ray system. These cables also create impediments to moving other devices (such as surgical tables, as well as specialized equipment such as mobile arthroscopic camera and display systems) and medical personnel around the room. With many medical procedures requiring the use of several different specialized, wheeled, mobile medical devices at various times during a medical procedure, the amount of cabling draped across the floor can become a hazard for medical personnel and cause great difficult in moving devices around the room. A third problem with some of these conventional x-ray systems is their limited motion during operation. In particular, the systems in FIG. 14 only function in the normal upright mode, or rotated around a single axis of rotation. There is no nod or tilt angle adjustment for the arms containing the x-ray source and detector, nor is there any means to swing or yaw the orientation of the C-arm around a vertical axis. These limited degrees of motion create additional difficulty in positioning the X-ray system to obtain the optimal images needed to diagnose or to assess progress during a medical procedure.

Figure 4:
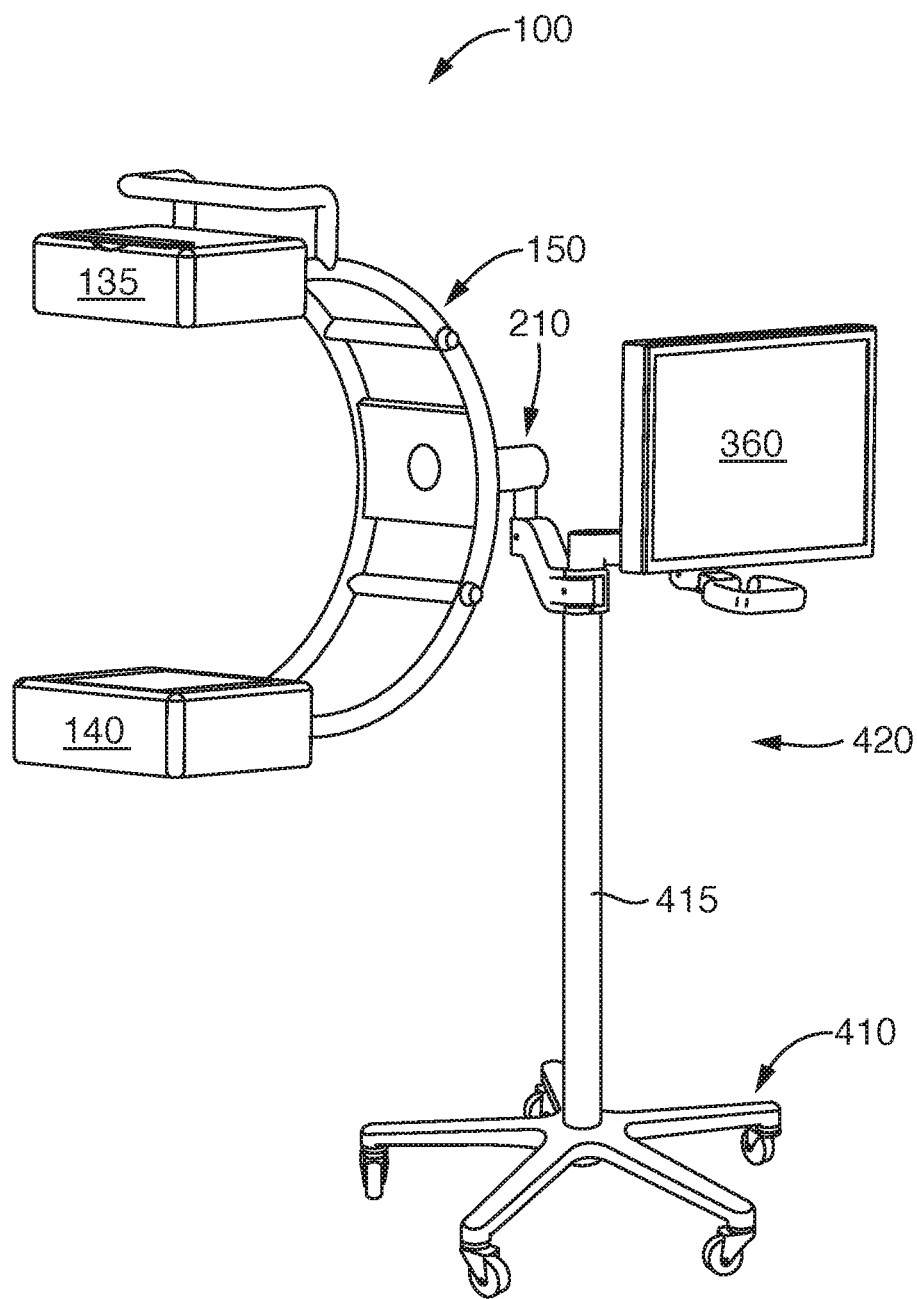
FIG. 4 shows other embodiments of supporting devices that can be used with small, portable X-ray devices.

In other configurations, though, the portable x-ray device 100 can be connected to a movable support structure. In such configurations, the movable support structure can be configured to move across a floor while supporting the x-ray device 100. Thus, the movable support structure can comprise one or more wheels, shelves, handles, monitors, computers, stabilizing members, limbs, legs, struts, cables, and/or weights (to counterbalance the weight of the imaging arm and/or any other component and prevent tipping the movable support structure). FIG. 4 shows some embodiments in which the movable support structure 420 comprises a wheeled structure 410 connected to a stand 415 that contains the tri-joint 210 that is connected to the x-ray device 100.

In some configurations, the X-ray device 100 and/or the external support structure can comprise any suitable locking mechanism that can selectively lock and unlock the rotation of the C-arm 105 around the object. For instance, the locking mechanism can comprise a manually-engaged clamp, a detent mechanism, a motorized lock, an electric lock, a radio controlled lock, a remotely engaged clamp, and/or any other suitable mechanism that can be used to lock and release the orbital rotation of the c-arm. In some configurations, the locking mechanism can be part of the tri-joint described herein or even an interface between the x-ray device 100 and the tri-joint.

In other embodiments, the portable x-ray device 100 can be connected to an external (or support) structure to form x-ray systems that are lighter and easier to move. In these embodiments, the x-ray systems contain numerous joints between the various components of the x-ray system, giving the systems more movement flexibility. These x-ray systems also do not require data, control, or power cables, making them truly mobile. This lack of cables also allows larger range of motion and movement angles for the x-ray device, as well as making it significantly easier to position the support structure and the x-ray C-arm as desired to obtain the optimum x-ray images. Being lighter and smaller makes the x-ray systems easier to move across the floor so that they can be easily positioned and manipulated during a surgical and/or imaging procedure.

Figure 5:
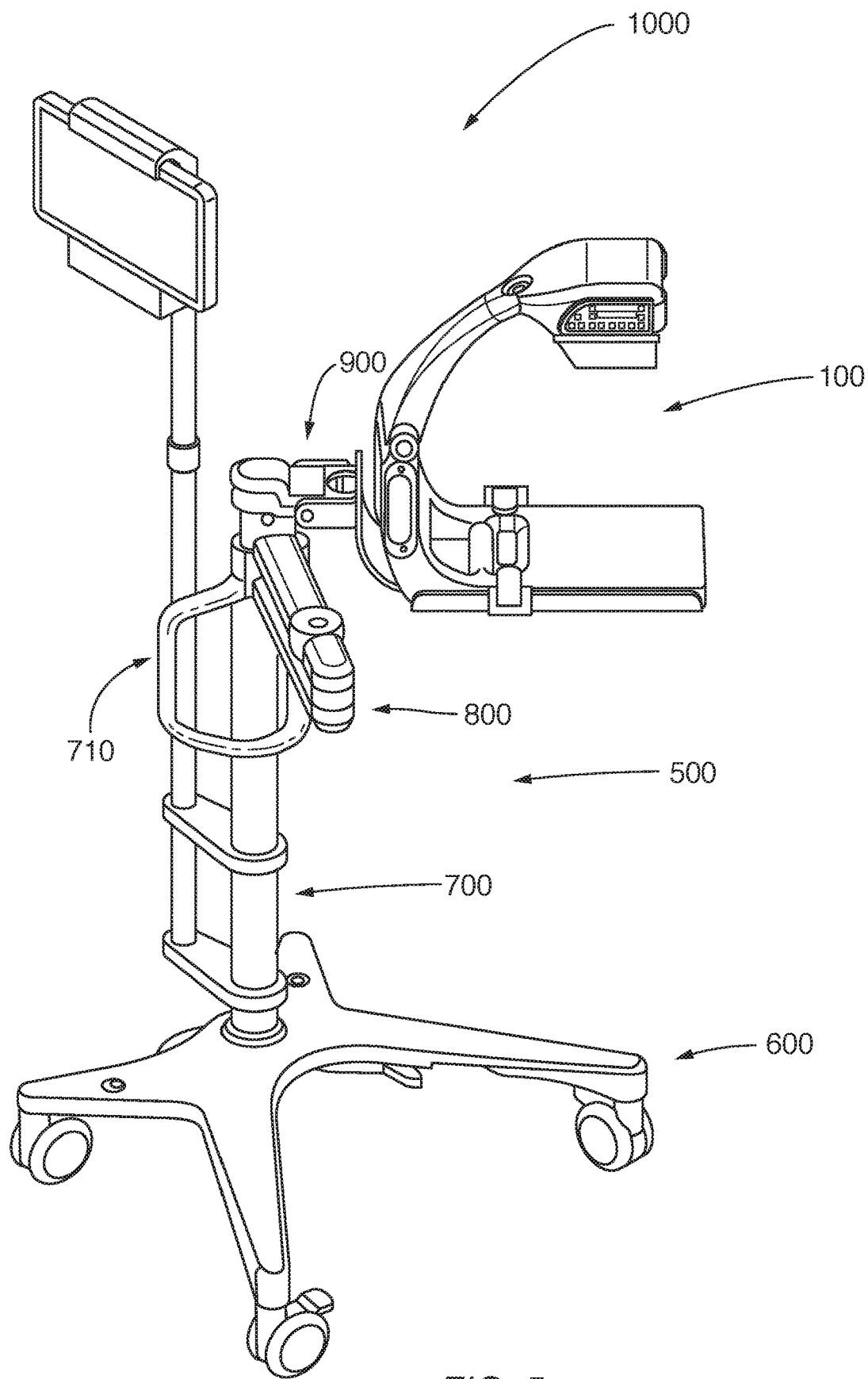
FIG. 5 illustrates yet other embodiments of supporting devices for holding small, portable X-ray devices.

Some examples of these x-ray systems are shown in FIGS. 5-13. As shown in FIG. 5, the x-ray systems 1000 contain a portable x-ray device 100 that is connected mechanically to a supporting device 500. The supporting device 500 contains a mobile base 600, an adjustable member 700 extending from the mobile base 600, an extension arm 800 connected to the adjustable member, and a connecting member 900 between the extension arm 800 and the portable x-ray device 100. Together, the supporting device 500 and the portable x-ray device 100 combine to form the x-ray system 1000. In some embodiments, the supporting device 500 can weigh from about 40 to about 200 pounds. In other embodiments, the supporting device 500 can weigh from about 50 to about 125 pounds. Since the portable x-ray device 100 can weigh about 10 to 25 pounds, in some embodiments, the x-ray system 1000 can weigh from about 60 to about 250 pounds. In other embodiments, the x-ray system 1000 can weigh from about 50 to about 210 pounds.

As shown in FIG. 5, the mobile base (or mobile base unit) 600 of the supporting device is configured so that the entire x-ray system 1000 is both mobile and stable for an operator (i.e., a medical professional) when the portable x-ray device 100 is attached (and detached) from the supporting device 500, as well as when the portable x-ray device 100 is operated to analyze a patient. In some embodiments, the mobile base 600 contains multiple legs 610 extending outward from a center point. In the embodiments shown in FIG. 6, the mobile base contains 4 legs 610 extending outward. The legs 610 can be configured with similar or dissimilar lengths and/or heights, provided that the support device 500 exhibits the needed mobility and stability. The legs 610 of the mobile base 600 can contain wheels 620 at the ends thereof, with an optional locking mechanism for each wheel, or for the base as a whole, that can be locked to keep the supporting device from moving.

Figure 6A:
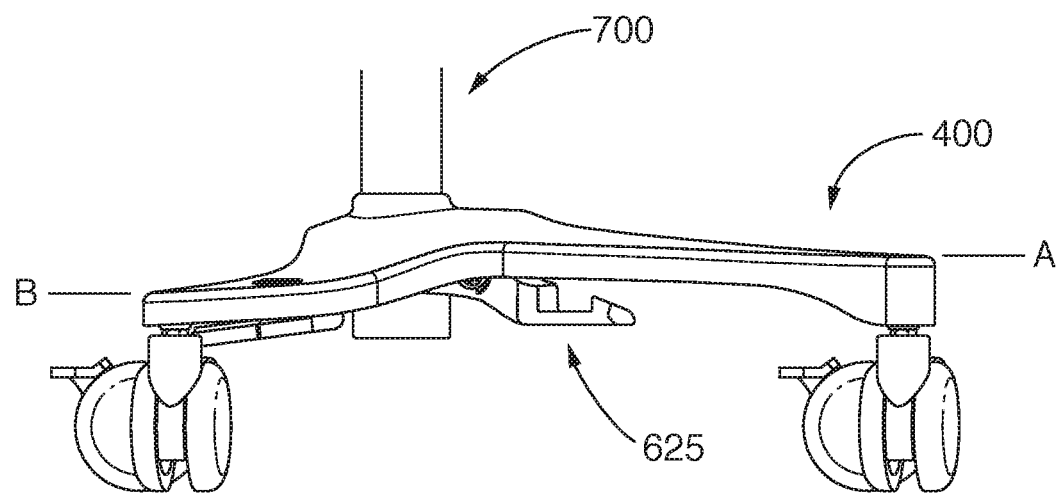
FIGS. 6A-6C show some embodiments of a mobile base unit of the supporting devices.
Figure 6B:
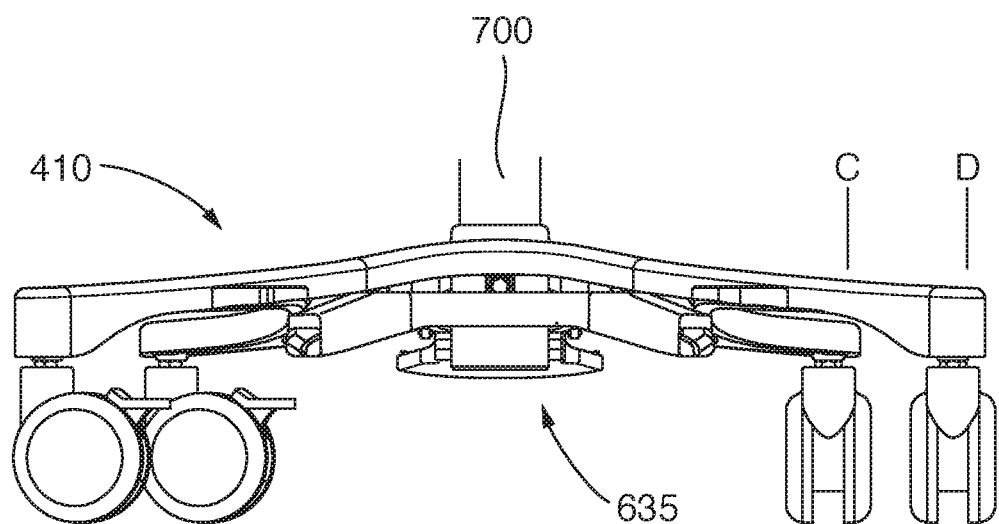
Figure 6C:
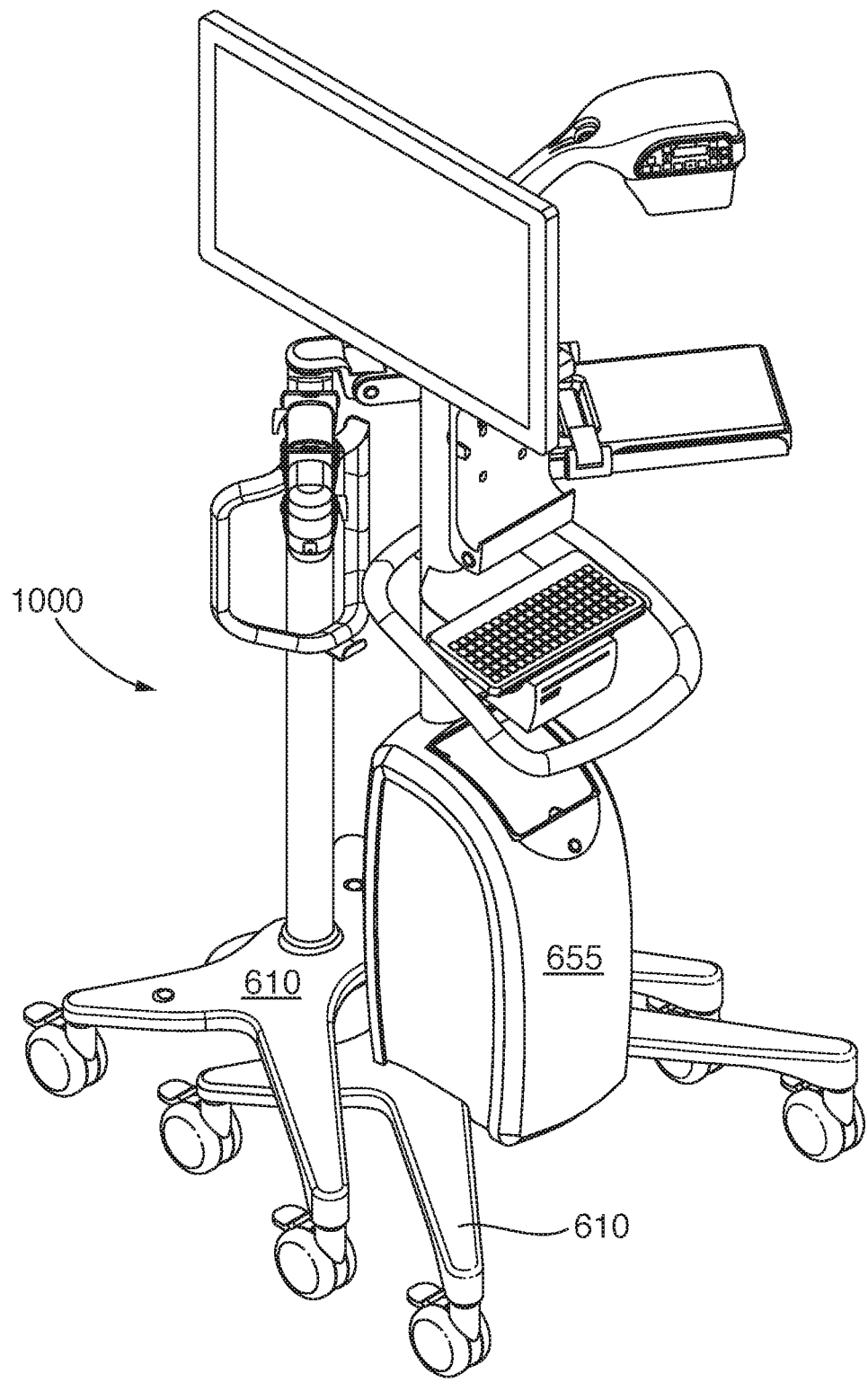

In some configurations, the legs 610 of the mobile base 600 can be configured to have a nestable configuration, as shown in FIGS. 6A though 6C. In these embodiments, a set of legs 610 extending in one direction have a shorter length and a shorter height than the other set of legs that extend in the opposite direction. As seen in FIG. 6A, the set of legs extending in one direction have a height A while the legs generally extending in an opposite direction have a height B that is lower than height A. As seen in the side view of FIG. 6B, the set of legs extending in one direction have a length C while the legs generally extending in an opposite direction have a length D that is longer than length C. Such a configuration allows the two sets of legs to mesh together in the nesting configuration as can be seen in FIG. 6B. A perspective view of this nesting configuration is depicted in FIG. 6C where a support stand with a monitor cart 655 is shown nested with the x-ray system 1000 so that their respective legs are nested together. This nesting configuration can be extended to other embodiments where the mobile base 600 contains more or less than 4 legs.

To help form this nesting configuration, the mobile base unit 600 can contain a catch mechanism which can used automatically to attach and lock the legs 610 together. One example of this catch mechanism is depicted as catch 625 in FIG. 6A. And to help release this nesting configuration, the mobile base unit 600 can contain a release mechanism which can be activated by a user to release the legs 610 from each other. One example of this release mechanism is depicted as release 635 in FIG. 6B.

The supporting device 500 also contains an adjustable member 700 that extends substantially vertically at one end from the mobile base 600 and the other end is connected to the extension arm 800. While FIG. 5 shows that adjustable member 700 extends vertically, the supporting device 500 can be configured so that the adjustable member 700 extends only mostly vertically, for example, at an angle of up to about 10 degrees from an exact vertical orientation. As well, while FIG. 5 shows that the adjustable member 700 is substantially straight, it can be configured with bends and/or twists along its length. In some configurations, the adjustable member 700 can contain a handle 710 (or multiple handles) which can be positioned anywhere along the length of the adjustable member 700. The height of the adjustable member 700 can be adjusted as needed by the operator. This height adjustment can be made by using a telescoping rod or other similar mechanism in the adjustable member.

In some configurations, the height of the adjustable member 700 of the supporting device 500 can be adjusted depending on the use of the portable x-ray device 100. For example, the x-ray system 1000 will often be used in a medical office or operating room so that the portable x-ray device 100 can be used in imaging a patient. Thus, the height of the adjustable member 700 can be adjusted so that the portable x-ray device 100 can be located near the patient, whether the patient is on a chair or a table, and whether the surgeon is standing or sitting during the procedure.

Figure 7:
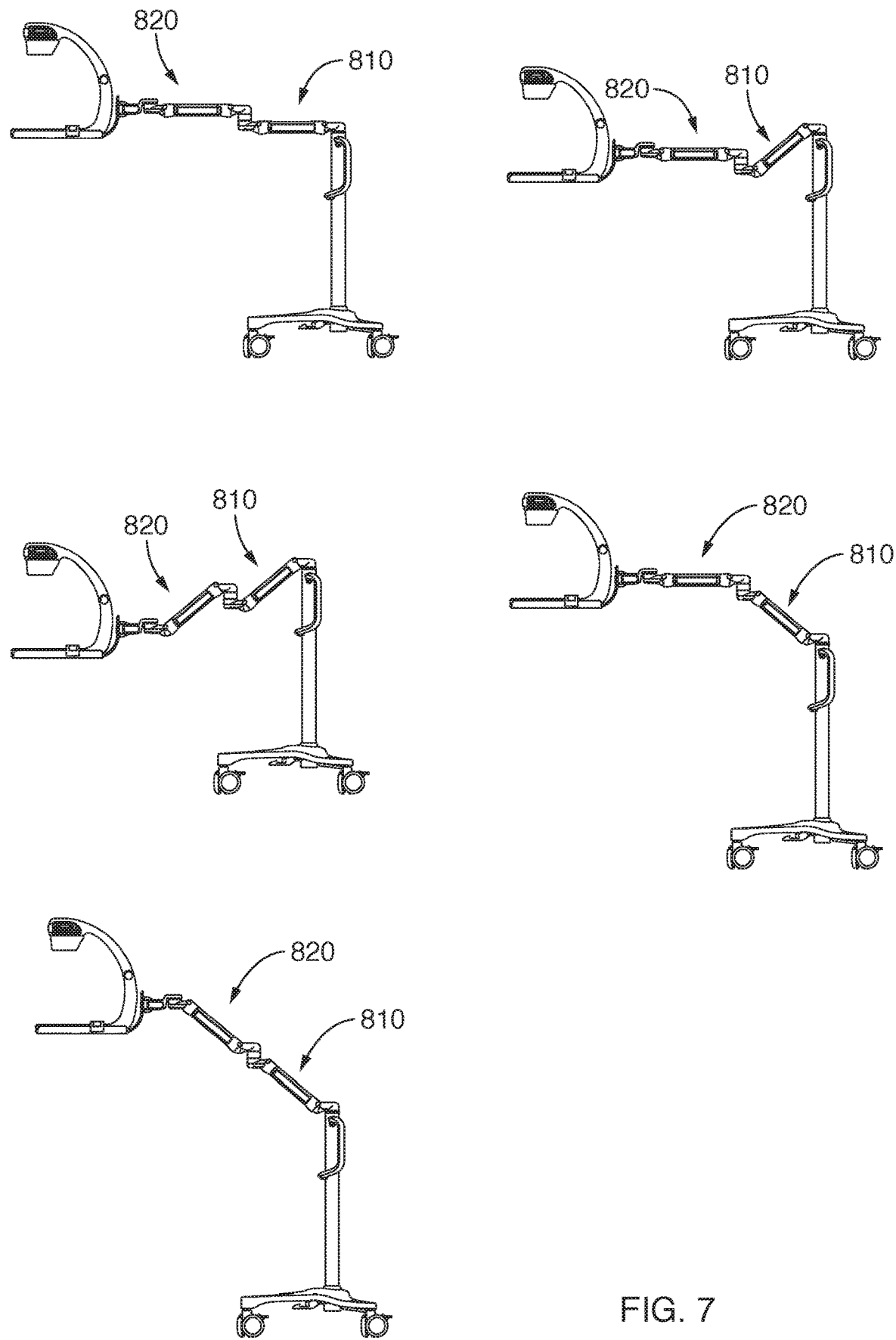
FIGS. 7-8 show various configurations of the extension arms of the supporting device.
Figure 8:
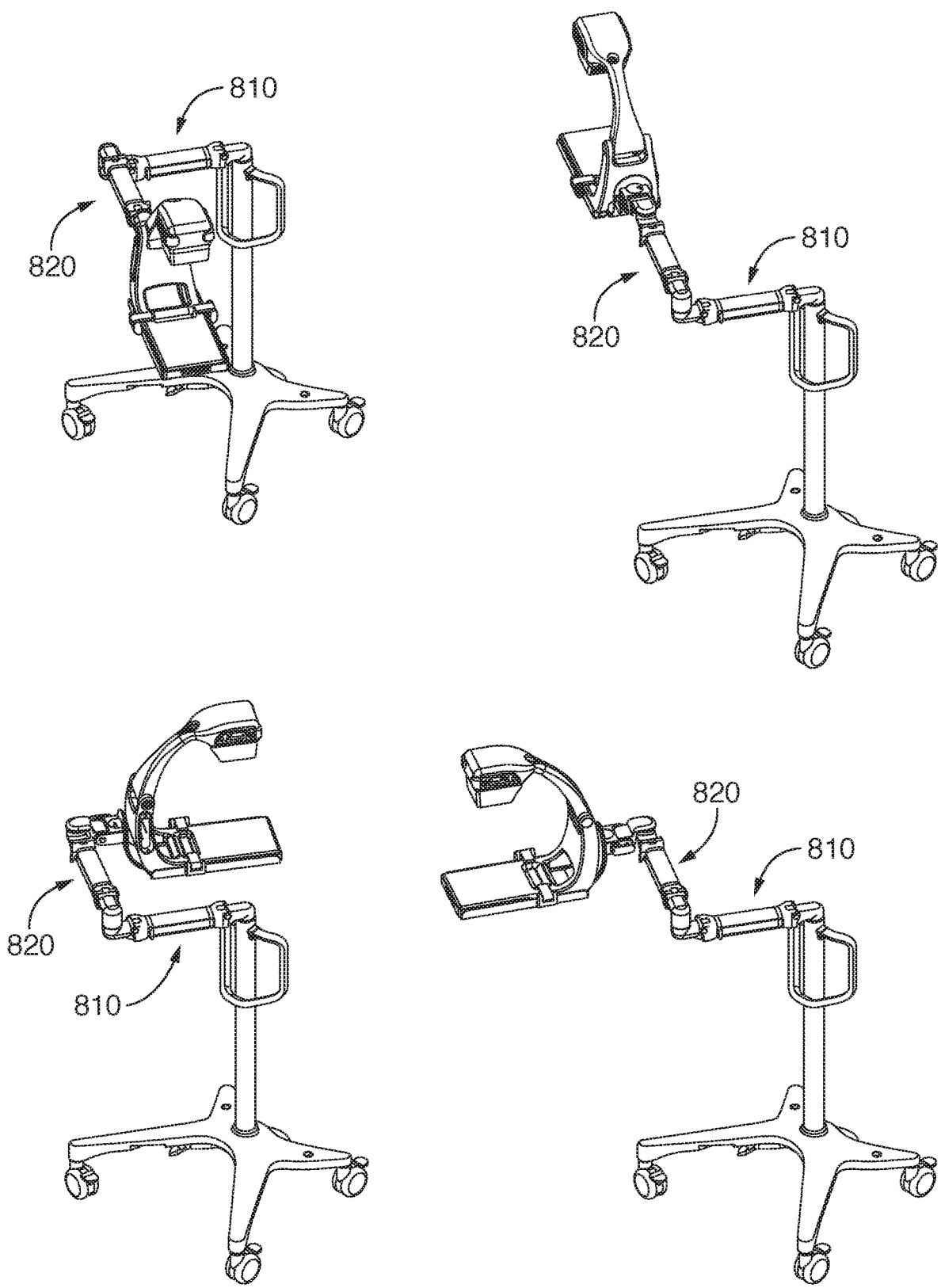

The supporting device 500 also contains an extension arm 800 that is connected to an end of the adjustable member 700. The extension arm 800 is configured so it is collapsible and hinged so it can extend in any combination of both vertical and horizontal directions. FIG. 5 shows the extension arm 800 in a collapsed configuration where the first part 810 and the second part 820 of the extension arm 800 are folded on top of each other. The first part 810 and the second part 820 are connected together with a hinge. Some of the possible extended configurations for the extension arm are shown in FIG. 7. These configurations demonstrate the extensions possible when both the first part 810 and the second part 820 of the extension 800 arm are extended in substantially the same direction. Some additional extended configurations are shown in FIG. 8. These configurations demonstrate the extensions possible when the first part 810 and the second part 820 of the extension arm 800 do not extend in substantially the same direction. Numerous other configurations are possible since the first part 810 and the second part 820 of the extension arm 800 are hinged and can move separate from each other. In other configurations (not shown), the extension arms can have additional third, fourth, etc. . . . parts that are hinged to each other.

The extension arm 800, the base 600, and the adjustable member 700 together can also be configured to be counterbalanced to provide stability for the x-ray system 1000 as the extension arm 800 moves throughout its considerable range of motion. The counterbalance mechanism can comprise any suitable component that allows it to substantially counterbalance the weight of the C-arm and the arms when extended away from the adjustable member 700. When the weight of the portable x-ray device 100 ranges between approximately 10 lbs (4.5 Kg) to approximately 25 lbs (11 Kg) along with the additional weight of the arms, the triple joint, the cradle 910, and the connecting member 900, the counterbalance weight can be upwards of 40 lbs, 50 lbs, 60 lbs, 70 lbs, or more, depending on where it is located on or in the support structure. In addition to mass, the counterbalance mechanisms can comprise one or more constant force springs, spring motors, gas springs, tension springs, torsion springs, compression springs, cams, hydraulic circuits, weights, and/or pulleys and a cable, with the spring forces or tensions of 10, 15, 20, 25, or perhaps even 30 Newtons or more, using known techniques. Along with these counterbalance mechanisms, locking mechanisms can be incorporated within them so that the extension arm 800 may be locked into the desired position for the portable x-ray device 100. Alternatively, the joints or hinges contained within the arm 800 and its parts 810 and 820 may have damping mechanisms employed to reduce motion oscillations and to enable the extension arm 800 to hold the position of the x-ray device 100 as desired without resorting to locking mechanisms.

In the embodiments where counterbalance mechanisms are contained within the extension arm 800, damping mechanisms can be incorporated into the counterbalance mechanism. This configuration can help dampen any natural oscillation of the extension arm 800 that may occur due to its length and the forces involved in supporting the portable x-ray device 100. Damping mechanisms can also be incorporated for safety reasons when the x-ray device 100 is not mounted on the extension arm 800, or when the portable x-ray device 100 is removed from the arm 800 and the cradle 910. The forces in the counterbalance mechanisms could cause significant and rapid arm movements if the weight of the x-ray device 100 is removed, or when the arm position is locked, the x-ray device 100 is removed, and then the lock subsequently released. If these movements are not dampened, it is possible that injury to the operator or others could be cause by these unexpected movements.

Figure 9:
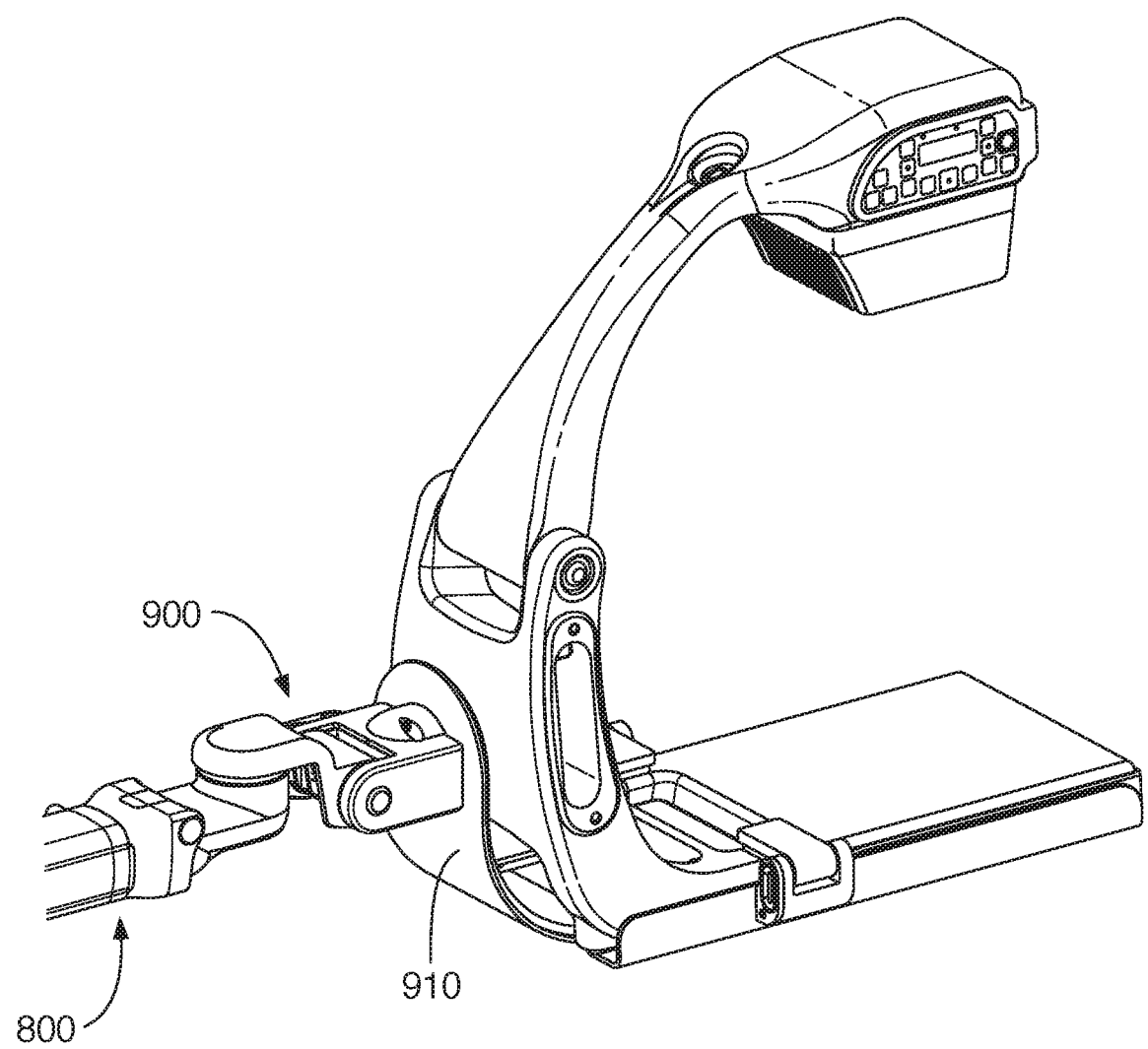
FIG. 9 shows some embodiments of a connecting member of the supporting devices.

The supporting device 500 also contains a connecting member 900 that is connected both to the extension arm 800 and to the portable x-ray device 100. As shown in FIG. 9, the end of the extension arm 800 can be connected to an end of the connecting member 900. The other end of the connecting member 900 can be connected to a cradle 910 into which the portable x-ray device 100 rests when it is attached. The portable x-ray device 100 can be attached and secured to the cradle 910 so that its position relative to the extension arm 800 is fixed during operation of the x-ray system 1000. Once operation of the x-ray system 1000 is concluded, the portable x-ray device 100 can be detached from the cradle 910 of the connecting member 900.

Figure 10:
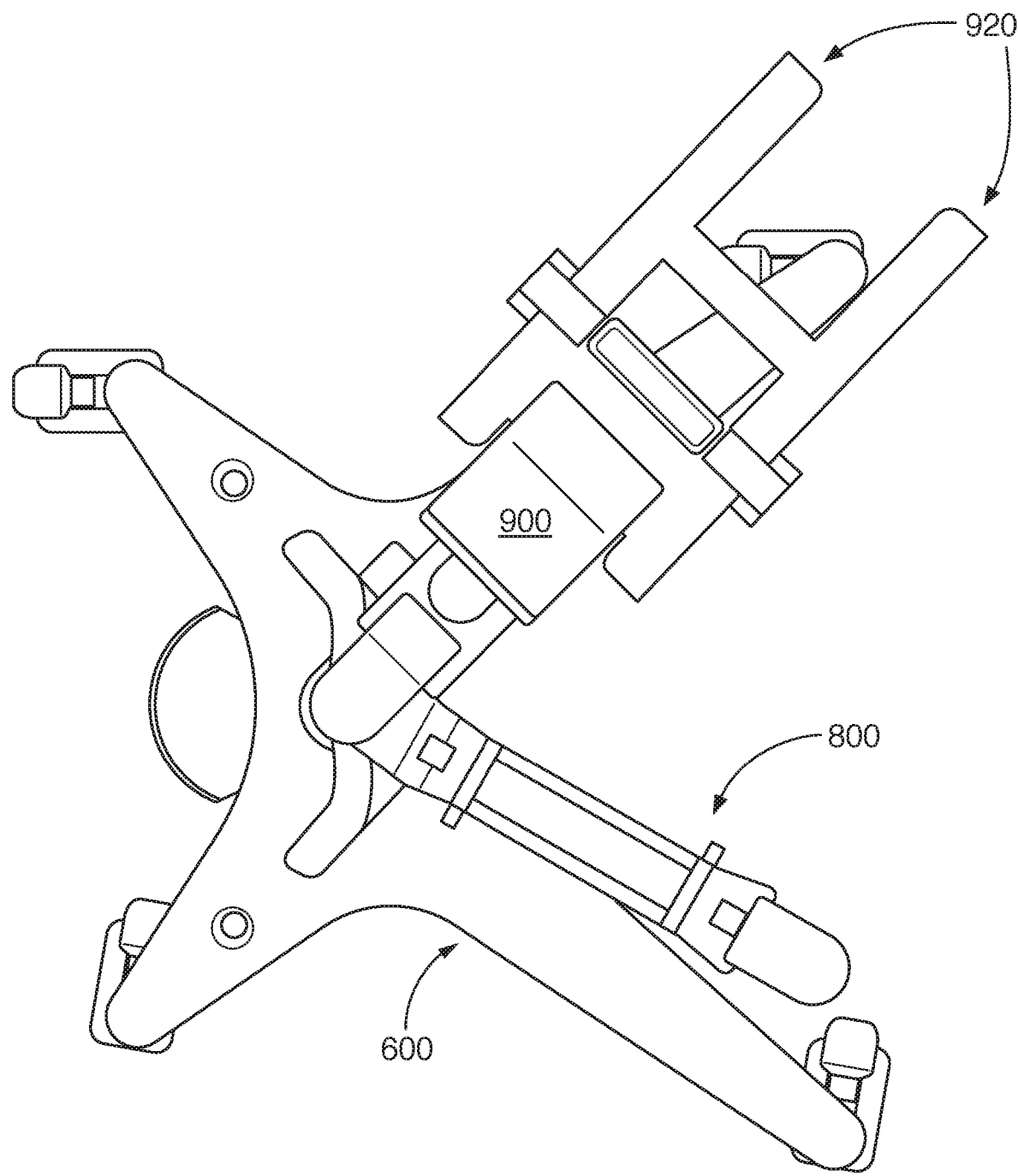
FIGS. 10-11 show other embodiments of a connecting member of the supporting devices.
Figure 11:
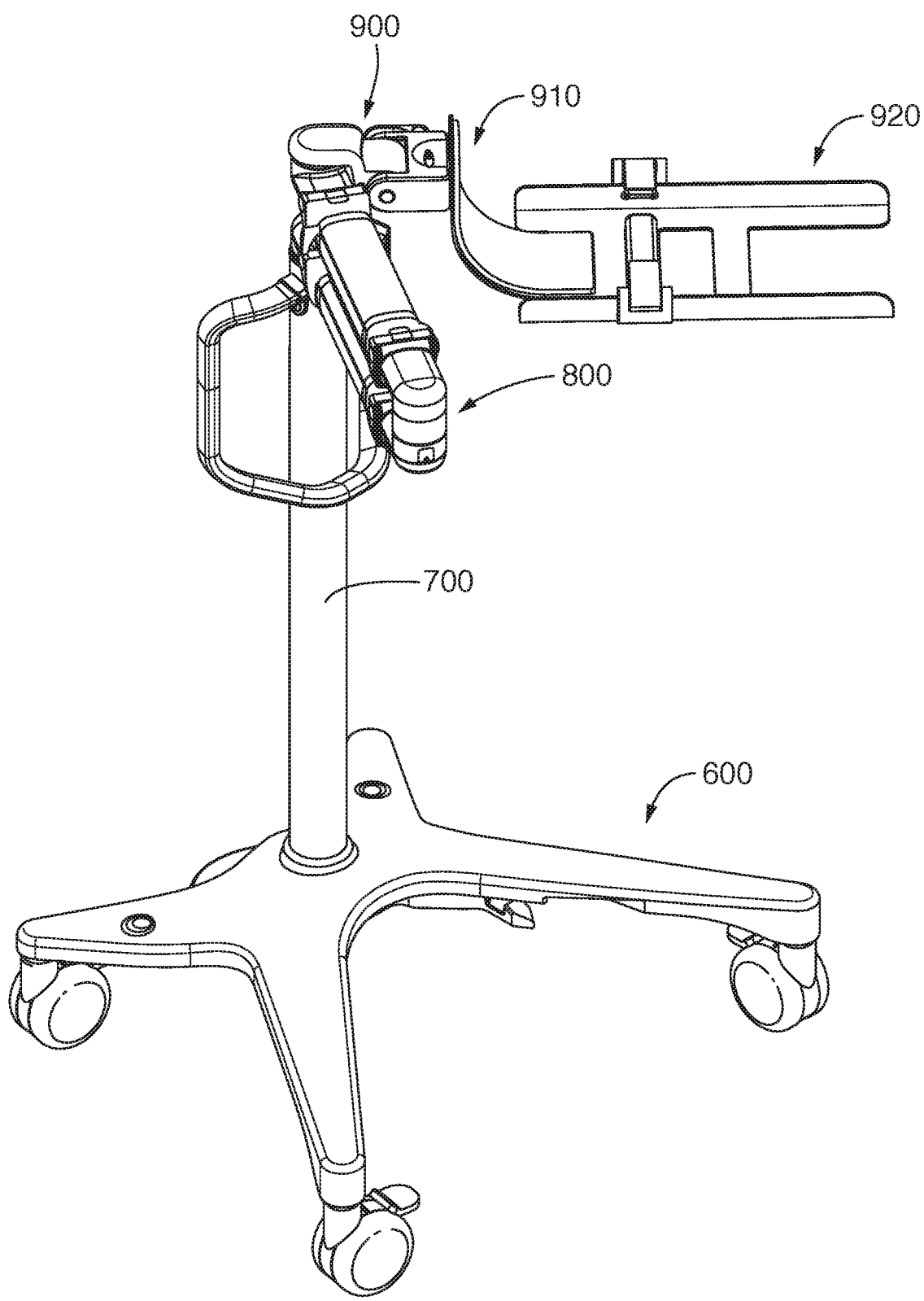

The connecting member 900 also contains mounting plate(s) 920 that are attached to the cradle 910 to provide a stable mounting support for the C-arm, as shown in the bottom view of the connecting member shown in FIG. 10 and the side view of FIG. 11. The configuration of the connecting member 900 with the cradle 910 and the mounting plates 920 allows a full 360 degrees of rotation, or even multiples of 360 degrees rotation, around a horizontal axis because there are no cables, wiring or other limitations on such motion due to the unique self-contained nature of the portable x-ray device 100. Similarly, the motions around the perpendicular horizontal axis (the head nodding motion) are not constrained by wires or cables, but only by the physical limitations of the cradle 910 and connecting member 900 impinging on the arms or other parts of the system at the extreme limits of the range of motion. Again in a similar fashion, the motion around a vertical axis (the directional or yaw motion) is also unconstrained except by the physical limitations of the cradle 910 and the connecting member 900. The configuration of the connecting member 900 also allows easy mounting of the portable x-ray device 100 since only a single person is needed to mount it because of its light weight and the manner in which the C-arm is mounted to the cradle 910.

Figure 12:
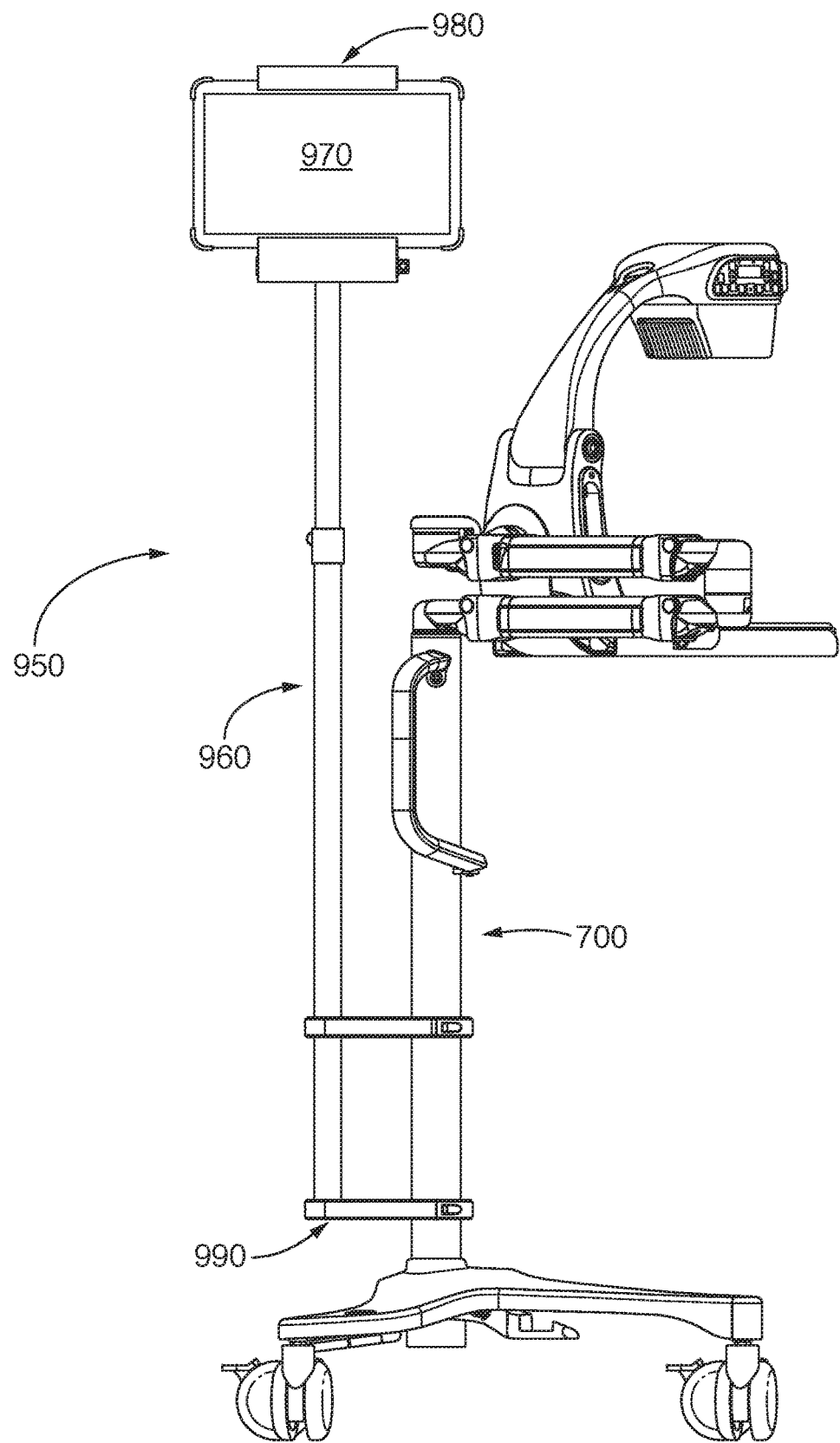
FIG. 12 shows some embodiments of an optional display unit that can be used with the supporting devices.

In some embodiments, the x-ray system 1000 contains an optional display support 950 that can be connected to the supporting device 500. As shown in FIG. 12, the display support 950 contains an adjustable arm 960 that is attached to a display device 970 or a holder 980 for a display device. The adjustable arm 960 of the display support 950 is attached to the adjustable member 700 of the support device 500 using two or more connectors 990 that encircle both the adjustable arm 960 and the adjustable member 700. Like the adjustable member 700 of the supporting device 500, the adjustable arm 960 extends substantially vertically. While FIG. 12 shows that the adjustable arm 960 extends vertically, the display support 950 can be configured so that the adjustable arm 960 extends only mostly vertically, for example, at a degree up to about 10 or 15 degrees from the exact vertical direction. As well, while FIG. 12 shows that the adjustable arm 960 is substantially straight, it can be configured with bends and/or twists along its length. The adjustable arm can be adjusted with, or separate from, the adjustable member 700 of the supporting device 500.

With the configurations described herein, x-ray system 1000 has a vertical and horizontal reach that is useful for medical personnel imaging a patient using the portable x-ray device 100. In some embodiments, the vertical range of the x-ray system 1000 can range from about 24 inches off the floor to a height of about 56 to 60 inches off the floor. In some embodiments, the horizontal reach of the extension arm 800 can range from a minimum of about 6 inches to a maximum of about 36 inches from the adjustable member 700. Longer horizontal reaches would be possible for the extension arm 800 provided that proper counterbalancing mechanisms are used.

The portable X-ray device 100 can be controlled by an operator, such as a clinician, a doctor, a radiologist, a technician, or other medically trained professionals and/or staff using any I/O mechanism. In some embodiments, the operator can control the X-ray device 100 at or from a central system control, such as a system control console adjacent the device, thereby making the operation of the system very easy. The operator can interface with the system control through a variety of optional user interfaces integrated with the I/O mechanism, or via an I/O mechanism that remains separate from the I/O mechanism. The control console, the user interface, or both can be located adjacent the X-ray device 100. In other embodiments, though, the control console and/or the user interface can be located remotely, such as in an adjacent room, so as to protect the operator from unnecessary exposure to X-rays.

As described above, the portable x-ray device 100 contains all of the power and electronics needed for operation internal to the device. Thus, there are no control, power, or data cables extend from the device 100 or the x-ray system 1000 containing the portable x-ray device 100. In some configurations, though, the supporting device 500 can contain internal electronics that provide additional data, power, or control connection to the portable x-ray device 100 and support the operation of the portable x-ray device 100.

The x-ray device 100 can also be connected to any type of electronic device with a wired or a wireless connection, even without the cradle 910. In these embodiments, the x-ray device can contain communication cables that connect the detector to the desired electronic device, such as a computer, which can be used to analyze or to manipulate the x-ray images from the detector. In other embodiments, however, the detector 140 can be connected with any wireless communications device that can be paired with the desired electronic device.

Figure 16:
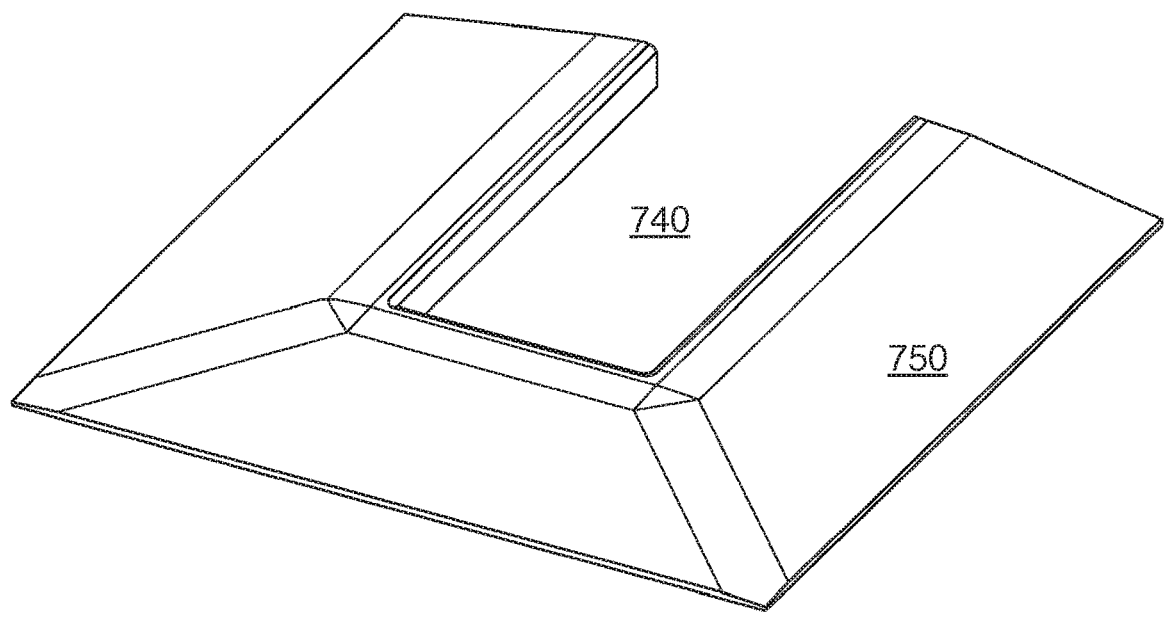
FIG. 16 shows some embodiments of using the supporting devices attached to portable x-ray devices with surgical tables.
Figure 16:
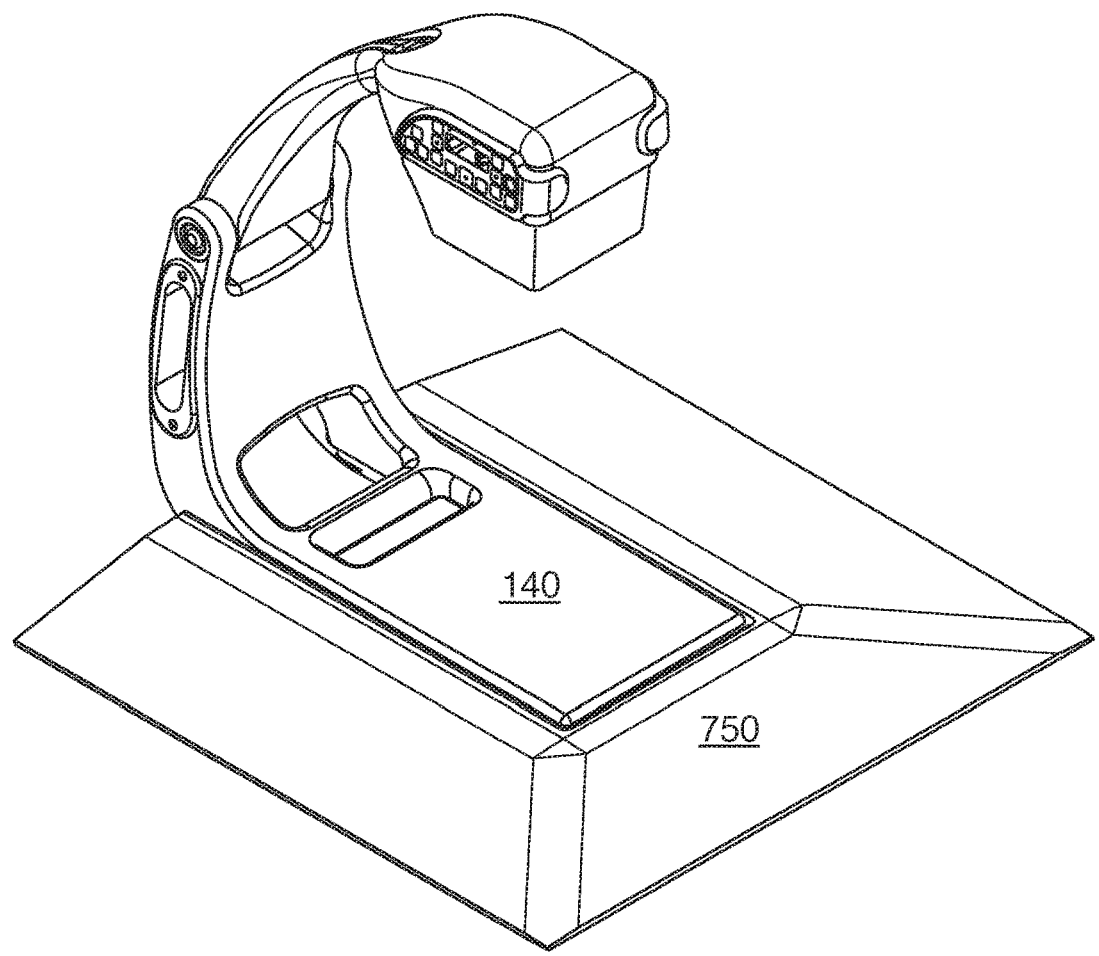

The portable X-ray device 100 can be configured to be integrated with an optional surgical table into which the x-ray system 1000 can slide or be inserted into. As shown in FIG. 16, the top of the x-ray detector 140 while attached to the supporting device 500 could be substantially planar with the top of surgical table 750, giving a larger platform to perform surgery right on the x-ray device 100 or after an optional protective covering is placed over the portable x-ray device 100. The table 750 can have any depth that is the substantially the same thickness as the x-ray detector 140. As shown in FIG. 16, a notch 740 can be cut into the table 750 into which the portable x-ray device 100 slides into, positioning the detector 140 at the center of the table 750. The table 750 can have tapered sides to minimize the patient discomfort when using it. Although not shown in FIG. 16, the table 750 could be configured to have a removable pad that would lift out and create a slot for the portable x-ray device 100 to slide into with the detector plate 140 positioned at the level of the top of the table 750. As well, a removable accessory platform that is attached to the table 750 could similarly provide for a slot to slide the portable x-ray device 100 into, allowing the patient's arm to be laid on a table that extends at right angles from the main structure of the table 750.

In other configurations, an actual slot in the top of an operating room table could be created. This slot could be filled with a blank during regular exams, but during imaging or a medical procedure, the blank could be removed and the portable x-ray device 100 could be positioned in the slot. The patient's anatomy could then be positioned on the detector 140 without having an extra platform, or the extra height of the detector, which would make it more uncomfortable. With such a configuration, if the patient's arm is lying flat along the table, it feels to the patient just like laying their arm (or leg) is flat along the table.

When in use, the x-ray system 1000 is easy and quick to use in several different modes. In a first mode, the portable x-ray device 100 can be removed from the supporting device 500 and used by medical personnel in a hand-held manner In this mode, the portable x-ray device 1000 can be used in a first location (i.e., with a first patient in a first room) and then carried by hand (without the supporting device 500) and used in a second location (i.e., with a second patient in a second room) a few moments later. Similarly, the portable x-ray device 100 can be used with a first supporting device 500 to image the first patient in the first room, detached from the first supporting device 500, carried by hand to a second room, connected to a second supporting device, and used to image the second patient.

In a second mode of operation, the portable x-ray device 100 (while being connected to the supporting device 500) can be used in a first location (i.e., with the first patient) and then the entire x-ray system can be wheeled and used in a second location (i.e., with the second patient). In this second mode of operation, the x-ray system 1000 can be located in a first part of the first room to analyze a first part of a patient and then moved to a second part of the first room to analyze a second part of the same patient.

In a third mode of operation, the x-ray system 1000 can remain stationary in a given location. The height of the support device 500 can be raised or lowered to accommodate where the patient is located, such as a chair or a high table. The extension arm 800 can be collapsed or extended for the desired length, such as to reach closer or further away from the patient. And the portable x-ray device 100 can be rotated in any of the three degrees of rotation (x, y, and z) to image any desired part of the patient quickly and effectively while also positioning the portable x-ray device 100 to allow for the presence of medical personnel, such as a surgeon and his assistant, around the patient and the portable x-ray device 100 at the same time. If needed, the entire x-ray system 1000 can be moved quickly a few inches or feet with minimal effort by the medical personnel to provide better access to the patient and the surgical field. And, of course, the entire x-ray system 1000 can also be easily moved a few inches or feet to bring it back into the desired position again.

Figure 13A:
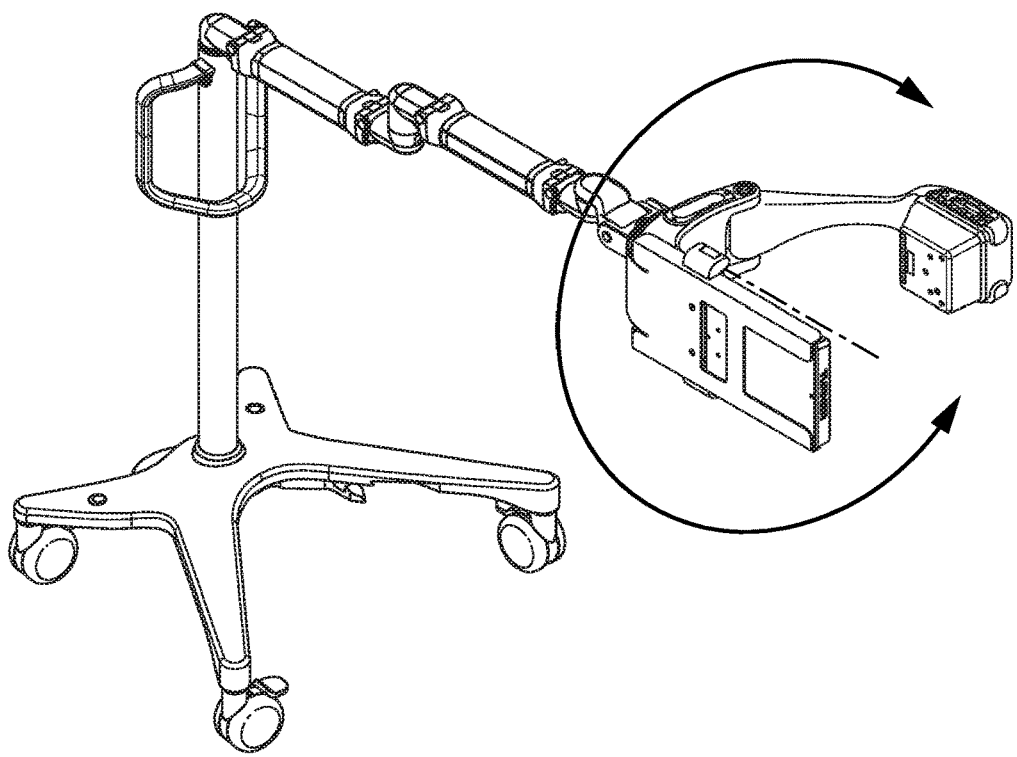
FIGS. 13A, B, and C shows some embodiments of the rotation of the portable x-ray devices when attached to the supporting device.

When the x-ray device 100 is connected to an external structure (including the supporting device 500), the C-shaped support arm 105 is capable of rotating around an object to be analyzed that remains in a fixed location. As illustrated in FIG. 13A, an operator can rotate the C-arm 105 of the portable x-ray device 100 by grabbing any part of the frame 150 and rotating the arm clockwise and/or counter-clockwise while part of the patient remains substantially immobile in the middle of the C-arm 105, as shown by the rotation arrow. The operator can selectively lock the C-arm at any suitable location in its rotation and/or release the rotation of the c-arm 105 by locking (or releasing) a locking mechanism.

Figure 13B:
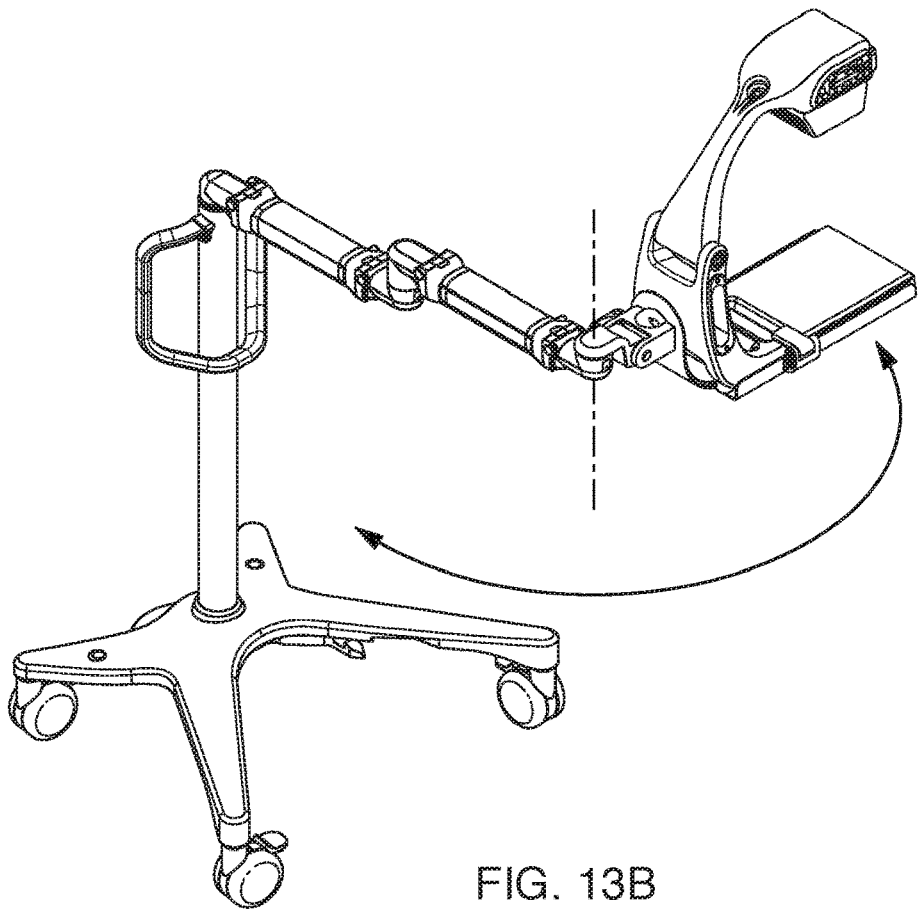
Figure 13C:
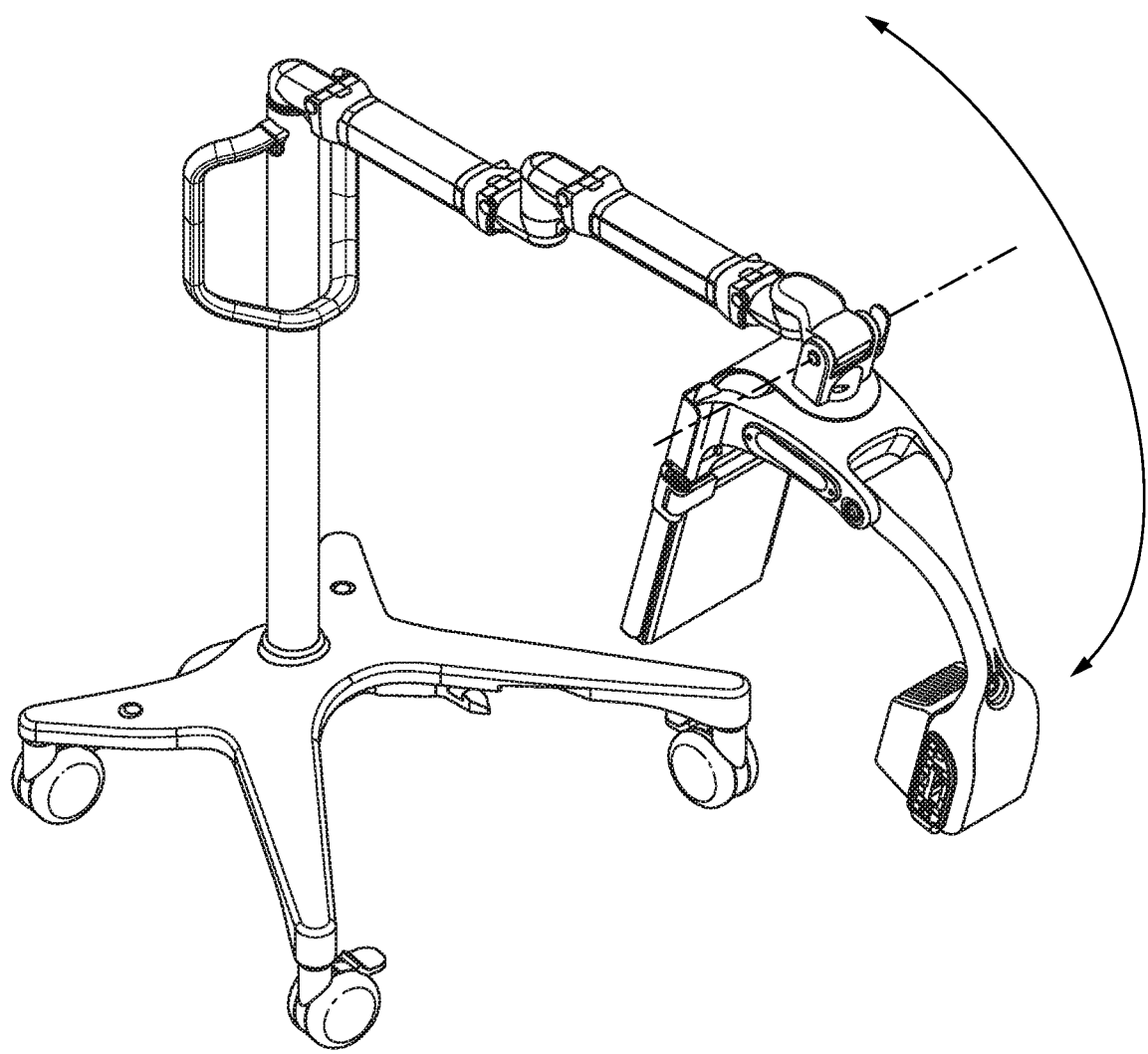

The portable x-ray device 100 can also rotate in other directions while attached to the supporting device. As shown in FIG. 13B, the portable x-ray device 100 can rotate horizontally as shown by the arrow. During the rotation in this horizontal direction, the portable x-ray device 100 can't be used to image a patient. As well, as shown in FIG. 13C, the portable x-ray device 100 can rotate in a vertical direction, or nodding direction, similar to nodding the head. During rotation in this vertical direction, the portable x-ray device can continue to image the patient for small adjustments, but for larger rotations an adjustment of the patient position might be required (depending on how the x-ray device 100 is mounted relative to the center of the vertical arc) in order to maintain the desired field of view.

In some embodiments, the X-ray system 1000 can be configured to allow the use of sterile coverings or drapes on the support structure and over the C-arm 105 to provide the sterility of the device that is necessary in many surgical procedures. Many components of the x-ray system 1000 have been designed to allow the successful use of these sterile coverings. A primary consideration for the use of sterile drapes is that the surfaces, locking handles, clamping mechanisms for securing the C-arm, the hinges and extendable adjustable arms, the triple joint, and all other features that are located, or potentially located, such that they could potentially be found within the surgical field, must be shaped and configure so that there is no sharp corners or other feature that could conceivably trap, catch, cut, or tear a surgical drape.

Using the x-ray systems 1000 containing a supporting device 500 with the portable x-ray device 100 provides numerous advantages over some conventional x-ray systems. The first advantage is that the X-ray systems 1000 are very easy to move since it is a very light-weight system. Thus, it "glides" or "dances" over the floor in comparison to some conventional systems because the x-ray systems 1000 are so much lighter.

The second advantage is that the X-ray systems 1000 are much easier to position when compared to the conventional systems shown in FIGS. 14 and 15. The x-ray systems 1000 are not as bulky as these conventional systems, and the x-ray systems 1000 can be positioned as desired to obtain the image without concern for where the display is positioned. Conventional all-in-one x-ray systems, such as those shown in FIG. 14 and FIG. 15, must be positioned not only so the C-arm x-ray source and detector are positioned to obtain a desirable or useful image, but so that the display must be in a location where it can be viewed by medical personnel. This requirement complicates the positioning of these conventional systems because the display can create an additional impediment to medical personnel walking around or by the x-ray system in order to accomplish their necessary tasks, as well as trying to position the display for viewing while also obtaining the viewing angle required for the images. Allowing the positioning of the X-ray C-arm independent of the image display allows a new degree of freedom in the use of x-ray imaging in the crowded and busy surgical environment.

The third advantage to these smaller, lighter, and easily-positioned x-ray systems 1000 is that they can be easier to manipulate during medical procedures. The standard use of some conventional x-ray systems, such as those illustrated in FIGS. 14-15, is to place them in the desired location with the c-arm in a specific position at the beginning of the procedure, and then leaving them in that location and position because moving them to a variety of positions is very difficult and time consuming But using the x-ray systems 1000 gives medical personnel the ability to move the x-ray system 1000 from location to location and the c-arm 105 from position to position, allowing them to make better surgical decisions and better validating their actions by taking images from more angles and orientations because it is easy and quick to do so.

As one example of this third advantage, the standard operating protocol for an arthroscopic examination or treatment of a knee requires that x-ray images be taken at multiple times spread throughout the entire procedure. These images are used for many purposes including monitoring progress, ensuring that needles, surgical screws, and pins are properly located, that bones or joint bearing surfaces are being properly modified by cutting, drilling, abrading, etc . . . , and verifying that the end results have positioned bone fragments, ligaments, and other surgical interventions properly. To accomplish these purposes, many conventional x-ray systems are put into position around the knee at the beginning of the procedure and not moved again because of their size, weight, complexity (including cabling), and the cumulative impact of all these factors requiring a major effort to move or reposition the system.

This effective immobility of these conventional x-ray systems leads to several undesirable consequences. The first is that the conventional x-ray system can become an undesired part of the sterile area immediately around the surgery. These conventional x-ray systems are, therefore, covered in sterile plastic drapes, and these drapes typically collect significant amounts of the saline fluid that is used to irrigate the knee during the procedure. It is not uncommon for multiple pints to quarts of fluid to collect in the folds of the surgical drape, requiring a careful clean-up after the procedure is complete.

Another undesired consequence is the limited views of the knee that can be obtained from these conventional x-ray systems when employed as described. Since it is undesirable during a procedure to expend the significant time required to move the x-ray system (because of collected fluids on the drapes over the device, the effective immobility of the conventional x-ray system, etc.), only one "camera angle" is typically used during the entire procedure, even though that angle may not be optimal for viewing the medically-vital issue at that moment.

Finally, the conventional x-ray system sources and detectors are in close proximity to the patient, and therefore impede the surgeon's and surgical assistant's access to the patient, especially from the left and right side. This impediment may lead to situations where the medical personnel, rather than moving the x-ray device and/or the x-ray system, may have to lift the knee up by hand to provide better access, it may require an adjustment of the operating room (OR) table or the stirrups holding the patients leg, or it may require the surgeon to assume a less comfortable or more-physically-strenuous stance with legs, back, arms, etc. to obtain the desired access to the patient and to achieve the necessary medical outcome.

All of these undesirable consequences can be reduced or eliminated by using the x-ray systems 1000, making the medical procedures quicker and more effective. The x-ray systems 1000 can be easily moved into place to obtain a desired set of images, just as easily moved away from the immediate vicinity of the surgery to allow better access by the surgeons and assistants, and then just as easily brought back in again. It is also advantageous since the x-ray system 1000 can be moved in from the top or front, rather than up from the bottom, as is required with typical conventional x-ray systems. If the necessary images are taken from the top or the front, then the x-ray system (though still covered in sterile drapes) does not collect body fluids, saline, and other detritus that must later be cleaned up or properly disposed of. Imaging from the top or the front is not possible with most conventional x-ray systems because of the significant effort and time required to move the system in and out for each image.

If the x-ray system can be easily moved in and out as described, then the "camera angle" can also be easily adjusted to provide the best and clearest view of the patient and the surgical situation as the procedure progresses. Rather than providing just one view throughout the procedure, it will be simple and easy to obtain views from a variety of angles with the x-ray system 1000 that is easy to move into place and reposition as required. Like with other medical devices, the concept of smaller and lighter x-ray imaging systems are always desired by medical personnel. But simply making the x-ray systems shown in FIGS. 14-15 smaller and lighter would not account for the advantages described herein (the impact on the patient, the surgeons, the medical procedure, and the clean-up afterwards). The advent of a small and easily-positioned x-ray system 1000 will change the paradigm of x-ray imaging and the way x-ray imaging is used to monitor medical procedures, leading to better outcomes for the patient.

And the x-ray systems 1000 have a very flexible, easily-positioned adjustable arm so the C-arm can be positioned, over, under, in front of, behind, or at any other desirable angle, to the object to be imaged (i.e., a patient). The X-ray systems 1000 can be easily moved into place to take an image and then easily moved out of the way of the medical procedure. And this process can easily be repeated multiple times during a procedure. The x-ray systems 1000 therefore make it quick and easy to take images at multiple orientations and angles during a surgical or medical procedure to better evaluate and diagnose the problem, monitor progress and changes during the procedure, and then to verify results, resulting in better information to the surgeon, and better outcomes for the patient. Testing of the X-ray system 1000 in simulated conditions indicate that it is possible to position and reposition the C-arm to obtain a new "camera angle" or a new view of the object to be imaged in 10 seconds or less, and that the X-ray system can be moved out of the way of the procedure in 15 seconds or less with ease. And as medical professionals become familiar with the X-ray system, it is believed that changing the viewing angle could be accomplished in 5 seconds or less, and the x-ray system 1000 could be moved out of the way or brought back into the surgical field again in possibly as little as 5 seconds or 7 seconds in some instances.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A supporting device for a portable X-ray device, comprising:
    a base unit containing multiple legs with different lengths and heights configured so that the legs have a nestable configuration;
    an adjustable member extending from the mobile base unit, the adjustable member configured with an adjustable height;
    an extension arm connected to the adjustable member, the extension arm configured to collapse toward and extend away from the adjustable member; and
    a connecting member configured to connect the extension arm with a portable x-ray device containing an x-ray source and an x-ray detector on a C-shaped support arm, the connecting member able to rotate up to 360 degrees in the x, y, or z direction, or any combination thereof.

2. The device of claim 1, wherein the legs of the base unit contain wheels so that the base unit is mobile.

3. The device of claim 1, wherein the supporting device contains no electrical power for the portable x-ray device.

4. The device of claim 1, wherein the portable x-ray device can be removed from the connecting member and operated independently by hand.

5. The device of claim 1, wherein the extension arm comprises two parts hinged together so that it can extend in any combination of vertical or horizontal directions.

6. The device of claim 1, wherein the connecting member comprises a cradle to which the portable x-ray device can be mounted.

7. The device of claim 1, further comprising a display support unit that can be connected to the adjustable member, wherein the display support contains an adjustable arm that is connected to a display device.

8. The device of claim 1, wherein the extension member comprises a counterbalancing mechanism.

9. A supporting device for a portable X-ray device, comprising:
- a base unit containing multiple legs with different lengths and heights configured so that the legs have a nestable configuration;
- an adjustable member extending from the mobile base unit, the adjustable member configured with an adjustable height;
- an extension arm connected to the adjustable member, the extension arm configured to collapse toward and extend away from the adjustable member; and
- a connecting member configured to connect the extension arm with a portable x-ray device, the portable x-ray device being removable from the connecting member and operated independently by hand.

10. The device of claim 9, wherein the legs of the base unit contain wheels so that the base unit is mobile.

11. The device of claim 9, wherein the supporting device contains no electrical power for the portable x-ray device.

12. The device of claim 9, wherein the connecting member can rotate up to 360 degrees in the x, y, or z direction, or any combination thereof.

13. The device of claim 9, wherein the extension arm comprises two parts hinged together so that it can extend in any combination of vertical or horizontal directions.

14. The device of claim 9, wherein the connecting member comprises a cradle to which the portable x-ray device can be mounted.

15. The device of claim 9, further comprising a display support unit that can be connected to the adjustable member, wherein the display support contains an adjustable arm that is connected to a display device.

16. The device of claim 9, wherein the extension member comprises a counterbalancing mechanism.

17. An x-ray system, comprising:
- a portable x-ray device with a C-shaped support arm, an X-ray source contained near one end of the support arm, and an X-ray detector contained near the other end of the support arm; and
- a supporting device comprising:
  - a base unit containing multiple legs with different lengths and heights configured so that the legs have a nestable configuration;
  - an adjustable member extending from the mobile base unit, the adjustable member configured with an adjustable height;
  - an extension arm connected to the adjustable member, the extension arm configured to collapse toward and extend away from the adjustable member; and
  - a connecting member configured to connect the extension arm with the support arm of portable x-ray device, the portable x-ray device being removable from the connecting member and operated independently by hand.

18. The system of claim 17, wherein the legs of the base unit contain wheels so that the base unit is mobile.

19. The system of claim 17, wherein the supporting device contains no electrical power for the portable x-ray device.

20. The device of claim 17, wherein the connecting member can rotate up to 360 degrees in the x, y, or z direction, or any combination thereof.

21. The device of claim 17, wherein the extension arm comprises two parts hinged together so that it can extend in any combination of vertical or horizontal directions.

* * * * *